(12) United States Patent
Higuchi et al.

(10) Patent No.: US 7,790,371 B2
(45) Date of Patent: Sep. 7, 2010

(54) ASSOCIATIONS OF POLYMORPHISMS IN THE FRZB GENE IN OBESITY AND OSTEOPOROSIS

(75) Inventors: Russell Gene Higuchi, Alameda, CA (US); Gary Allen Peltz, Redwood City, CA (US); Bonnie Fijal, Hillsborough, NJ (US); Sunhee Kwon Ro, Foster City, CA (US); Jia Li, Union City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 215 days.

(21) Appl. No.: 10/552,641

(22) PCT Filed: Apr. 20, 2004

(86) PCT No.: PCT/EP2004/004178

§ 371 (c)(1), (2), (4) Date: Oct. 7, 2005

(87) PCT Pub. No.: WO2004/094659

PCT Pub. Date: Nov. 4, 2004

(65) Prior Publication Data

US 2006/0204965 A1  Sep. 14, 2006

Related U.S. Application Data

(60) Provisional application No. 60/464,372, filed on Apr. 21, 2003, provisional application No. 60/526,689, filed on Dec. 2, 2003.

(51) Int. Cl.
*C12Q 1/68* (2006.01)
*C12P 19/34* (2006.01)
(52) U.S. Cl. .......................... 435/6; 435/91.2
(58) Field of Classification Search .................. None
See application file for complete search history.

(56) References Cited

U.S. PATENT DOCUMENTS

| 6,479,242 B1 | 11/2002 | Guo et al. |
| 2002/0182616 A1 | 12/2002 | Wuhlestedt et al. |
| 2002/0182622 A1 | 12/2002 | Nakamura et al. |

FOREIGN PATENT DOCUMENTS

WO   WO 02/083839 A2   10/2002

OTHER PUBLICATIONS

Ikegawa et al., Curr Opin Rheumatol, 2007, 19(5):429-434.*
Hegele, Arterioscler. Thromb. Vasc. Biol (2002, vol. 22, pp. 1058-1061.*
Hattersley et al. Lancet, 2005, vol. 366, pp. 1315-1323.*
Ionnidis Plost Med, 2005, 2(8):e124.*
Kroese et al. Genetics in Medicine, vol. 6 (2004), p. 475-480.*
Frizzled related protein gene, GeneCard, pp. 1-15, available at www.genecard.com.*
Mummidi et al. J. Biol. Chem, 2000, vol. 275, pp. 18946-18961.*
Acuña, G., et al., (2002), "Pharmacogenetic analysis of adverse drug effect reveals genetic variant for susceptibility to liver toxicity", *The Pharmacogenomics Journal*, 2: 227-234.
Germer, S., et al., (2002), "High-Throughput SNP Allele-Frequency Determination in Pooled DNA Samples by Kinetic PCR", *Genomic Research*, 10: 258-266.
Leyns, L., et al., (1997), "FRZB-1 s a secreted antagonist of Wnt Signaling Expressed in the Spemann Organizer", *Cell*, 88:747-756.
Schumann, H., et al., (2000), "Expression of secreted frizzled related proteins 3 and 4 in human ventricular myocardium correlates with apoptosis related gene expression", *Cardiovascular Research* 45: 720-728.

* cited by examiner

*Primary Examiner*—Sarae Bausch
(74) *Attorney, Agent, or Firm*—Olga Kay; Robert W. Marin

(57) ABSTRACT

The present invention relates to polymorphisms of the FRZB gene and the analysis of nucleic acids thereof. The invention further relates to methods of predicting risks of certain conditions in individual and kits for the determination of such risks.

12 Claims, 1 Drawing Sheet

| | | | |
|---|---|---|---|
| 5'TGTCGTCTG<br>ACAGCAGAC5' | A | 5'TGTCATCTG<br>ACAGTAGAC5' | B |
| 5'TGTGCTTCA<br>ACACGAAGT5' | C | 5'TGTGTTTCA<br>ACACAAAGT5' | D |
| 5'AAAGACTCA<br>TTTCTGAGT5' | E | 5'AAAGCCTCA<br>TTTCGGAGT5' | F |
| 5'TCAAAGCAG<br>AGTTTCGTC5' | G | 5'TCAATGCAG<br>AGTTACGTC5' | H |
| 5'CATTCGGGC<br>GTAAGCCCG5' | I | 5'CATTTGGGC<br>GTAAACCCG5' | J |
| 5'TATGCGTGT<br>ATACGCACA5' | K | 5'TATGTGTGT<br>ATACACACA5' | L |
| 5'ACATATAAG<br>TGTATATTC5' | M | 5'ACATGTAAG<br>TGTACATTC5' | N |
| 5'CCTTTAGTA<br>GGAAATCAT5' | O | 5'CCTTCAGTA<br>GGAAGTCAT5' | P |
| 5'AGCACGCAA<br>TCGTGCGTT5' | Q | 5'AGCAGGCAA<br>TCGTCCGTT5' | R |
| 5'TTAAGTATA<br>AATTCATAT5' | S | 5'TTAAATATA<br>AATTTATAT5' | T |
| 5'CCCATGAAT<br>GGGTACTTA5' | U | 5'CCCACGAAT<br>GGGTGCTTA5' | V |

FIG. 1

ASSOCIATIONS OF POLYMORPHISMS IN THE FRZB GENE IN OBESITY AND OSTEOPOROSIS

CROSS-REFERENCE TO RELATED APPLICATIONS

This application is a 371 application of international patent application PCT/EP2004/004178 filed Apr. 20, 2004, which claims priority to U.S. provisional patent application U.S. Ser. No. 60/464,372 filed Apr. 21, 2003 and U.S. provisional patent application U.S. Ser. No. 60/526,689 filed Dec. 2, 2003. The present application claims priority to, and benefit of, these applications, pursuant to 35 U. S. C. §119(e) and any other applicable statute or rule.

FIELD OF THE INVENTION

The invention relates to methods and reagents for detecting an individual's risk for obesity and/or osteoporosis. More specifically, it relates to methods and reagents for detecting an individual's increased or decreased risk for obesity and/or osteoporosis by identifying the presence of at least one polymorphism in the FRZB gene.

BACKGROUND OF THE INVENTION

Transplantation experiments by Spemann and Mangold (1924, *Arch. Mikroskopische Anat. Entwicklungsmechanik*, 100:599-638) established the presence of an anatomically discrete region, the Spemann organizer, or dorsal lip, that controls patterning of the developing body axis in vertebrate embryos. Diffusible factors emanating from this region were found to be involved in different developmental processes. The arrangement of Drosophila cuticle hairs in a defined polarity was found to be genetically controlled by 'frizzled' (FZD1), a 7-transmembrane receptor with a large extracellular cysteine-rich domain.

The bovine and human homologs of FZD1 were cloned by RT-PCR and by screening bovine articular cartilage and human placenta cDNA libraries, which identified cDNAs encoding FRZB, the mammalian analog of FZD1 (Hoang et al., 1996, *J. Biol. Chem.*, 271:26131-26137). The deduced 325-amino acid bovine and human FRZB proteins share 94% amino acid identity. Sequence analysis predicted that FRZB contains a 25-amino acid signal peptide, an N-terminal N-glycosylation site, a 24-amino acid putative transmembrane segment, a region with multiple potential Ser/Thr phosphorylation sites, and a serine-rich C-terminal domain. The N-terminal region of FRZB shares 50% amino acid identity, including the conservation of 10 Cys residues, with frizzled. Immunoblot analysis determined that FRZB is expressed as an approximately 36-kD protein. In situ hybridization analysis of human embryos representing different stages of development detected no expression from week 6 through week 13 except in the developing appendicular skeleton, as well as in several craniofacial bones and epiphyseal ends of the rib cage. Immunochemical analysis confirmed the expression of FRZB in the developing skeletal structures.

Northern blot analysis revealed that FRZB is expressed strongly in placenta and heart, at intermediate levels in brain, skeletal muscle, kidney, and pancreas, and at low levels in lung and liver (Leyns et al., 1997, *Cell* 88:747-756). SDS-PAGE analysis detected secretion of FRZB, possibly after proteolytic cleavage, consistent with FRZB's lack of the 7 transmembrane domains found in the Drosophila and vertebrate frizzled gene family. Functional analysis in Xenopus embryos showed that FRZB can antagonize the early and late effects of WNT8 signaling. Mammalian WNT genes include oncogenes that lead to mammary tumors. For further characterization of FRZB, see, e.g., Dann et al., 2001, *Nature* 412: 86-90; Rattner et al., 1997, *Proc. Nat. Acad. Sci.* 94:2859-2863; and Schumann et al., 2000, *Cardiovasc Res.* 45:720-728.

Leyns et al. (supra) mapped the human FRZB gene to 2q31-q33. They noted that loss of one copy of the 2q arm occurs with high incidence in lung and colorectal carcinomas, as well as in neuroblastomas, and suggested that FRZB might function as a tumor suppressor gene. Hoang et al. (supra) suggested FRZB might play a role in skeletal morphogenesis. However, a direct role for the FRZB gene in human disease and development has not been identified.

Among other aspects, the present invention provides alleles of FRZB, identified by the presence of one or more predisposing or protective polymorphisms, that are associated with an increased or decreased risk for obesity and/or osteoporosis. A complete understanding of the invention will be obtained upon review of the following.

SUMMARY OF THE INVENTION

The invention provides methods, reagents and kits for detecting an individual's increased or decreased risk for obesity and/or osteoporotic diseases and related diseases. In certain embodiments, the methods are used to determine an individual's risk for obesity and related diseases. In other embodiments, the methods are used to determine an individual's risk for osteoporosis and related diseases. In further embodiments, the methods of determining risk are combined with known clinical methods to diagnose osteoporosis or obesity.

A first general class of embodiments provides methods for determining an individual's risk for obesity. In the methods, presence of at least one obesity-related polymorphism in a frizzled-related protein (FRZB) gene in a nucleic acid sample of the individual is detected. The presence of the at least one polymorphism provides an indication of the individual's risk for obesity. The individual's risk for obesity can be, e.g., either an increased risk or a decreased risk as compared to an individual without the at least one polymorphism (e.g., an individual with a different allele at that polymorphic site). Accordingly, the at least one polymorphism can comprise a predisposing or a protective polymorphism in the FRZB gene.

The at least one polymorphism can comprise essentially any suitable polymorphism(s), including, but not limited to, restriction fragment length polymorphisms, random amplified polymorphic DNA, arbitrary fragment length polymorphisms, simple sequence repeats, single-stranded conformation polymorphisms, and amplified variable sequences. In a preferred class of embodiments, the at least one polymorphism comprises at least one single nucleotide polymorphism (SNP). For example, the polymorphism can be either allele of T2303723C, C18679T, G19524A, T19575G, T22242A, G23043A, G23415A, T23549C, A24791G, C26794G, or G27014A. In one class of embodiments, the at least one polymorphism is selected from the group consisting of: T allele of T2303723C, C allele of T2303723C, C allele of C18679T, T allele of C18679T, G allele of G19524A, A allele of G19524A, T allele of T22242A, A allele of T22242A, A allele of A24791G, and G allele of A24791G.

In one class of embodiments, the presence of two or more polymorphisms is detected (e.g., two or more polymorphisms at a single polymorphic site and/or at different polymorphic sites, e.g., a haplotype). At least one of the two or more polymorphisms (e.g., all of the polymorphisms) is optionally selected from the group consisting of: the T allele of T2303723C, the C allele of T2303723C, the C allele of C18679T, the T allele of C18679T, the G allele of G19524A, the A allele of G19524A, the T allele of T22242A, the A allele of T22242A, the A allele of A24791G, and the G allele of A24791G.

The nucleic acid sample typically comprises DNA or RNA. The presence of the at least one polymorphism in the nucleic acid sample can be detected by any of the variety of methods known in the art For example, the at least one polymorphism can be detected by sequencing, e.g., sequencing of the region of the FRZB gene including the polymorphic site(s). The region of FRZB is optionally amplified prior to the sequencing step. As another example, the at least one polymorphism is detected by amplification, e.g., of the region of the FRZB gene including the polymorphic site(s). The amplification can be, e.g., an allele-specific amplification. The amplification can comprise a polymerase chain reaction (e.g., kinetic PCR), a ligase chain reaction, or the like. As yet another example, the polymorphism can be detected by hybridization of a nucleic acid probe. Thus, in one class of embodiments, to detect the polymorphism the nucleic acid sample is contacted with at least one sequence-specific oligonucleotide under conditions (e.g., stringent conditions) that allow binding of the at least one oligonucleotide to the nucleic acid sample. The at least one sequence-specific oligonucleotide hybridizes under stringent conditions to a region of the FRZB gene comprising the at least one obesity-related polymorphism. Hybridization of the at least one oligonucleotide to the nucleic acid sample is then detected. In a related class of embodiments, the FRZB region comprising the polymorphism(s) is amplified prior to probe hybridization. Thus, in this class of embodiments, the nucleic acid sample is amplified to provide an amplified nucleic acid sample. The amplified nucleic acid sample is contacted with at least one sequence-specific oligonucleotide under conditions that allow binding of the oligonucleotide to the amplified nucleic acid sample (e.g., stringent conditions). The at least one sequence-specific oligonucleotide hybridizes under stringent conditions to a region of the FRZB gene comprising the at least one obesity-related polymorphism. Hybridization of the at least one sequence-specific oligonucleotide to the amplified nucleic acid sample is detected. The presence of the at least one obesity-related polymorphism can be, e.g., qualitatively or quantitatively detected.

In certain embodiments, the presence of the polymorphism inherited from one of the individual's parents provides an indication of the individual's risk for obesity (e.g., when the associated FRZB allele exerts a dominant effect, such that inheritance of the polymorphism from one parent is sufficiently predictive). In other embodiments, the presence of the polymorphism inherited from both of the individual's parents provides an indication of the individual's risk for obesity.

As noted, the methods are optionally combined with known clinical methods, e.g., to diagnose obesity. Thus, the methods optionally include performing at least one clinical test for obesity (e.g., determining a body mass index (BMI) of the individual).

A second general class of embodiments provides methods for determining an individual's risk for osteoporosis. In the methods, presence of at least one osteoporosis-related polymorphism in a frizzled-related protein (FRZB) gene in a nucleic acid sample of the individual is detected. The presence of the at least one polymorphism provides an indication of the individual's risk for osteoporosis. The individual's risk for osteoporosis can be, e.g., either an increased risk or a decreased risk as compared to an individual without the at least one polymorphism (e.g., an individual with a different allele at that polymorphic site). Accordingly, the at least one polymorphism can comprise a predisposing or a protective polymorphism in the FRZB gene.

The at least one polymorphism can comprise essentially any suitable polymorphism(s), including, but not limited to, restriction fragment length polymorphisms, random amplified polymorphic DNA, arbitrary fragment length polymorphisms, simple sequence repeats, single-stranded conformation polymorphisms, and amplified variable sequences. In a preferred class of embodiments, the at least one polymorphism comprises at least one single nucleotide polymorphism (SNP). For example, the polymorphism can be either allele of T2303723C, C18679T, G19524A, T19575G, T22242A, G23043A, G23415A, T23549C, A24791G, C26794G, or G27014A. In one class of embodiments, the at least one polymorphism is selected from the group consisting of: C allele of C18679T, T allele of C18679T, G allele of G19524A, A allele of G19524A, A allele of A24791G, G allele of A24791G, C allele of C26794G, G allele of C26794G, G allele of G27014A, and A allele of G27014A.

In one class of embodiments, the presence of two or more polymorphisms is detected (e.g., two or more polymorphisms at a single polymorphic site and/or at different polymorphic sites, e.g., a haplotype). At least one of the two or more polymorphisms (e.g., all of the polymorphisms) is optionally selected from the group consisting of: the C allele of C18679T, the T allele of C18679T, the G allele of G19524A, the A allele of G19524A, the A allele of A24791G, the G allele of A24791G, the C allele of C26794G, the G allele of C26794G, the G allele of G27014A, and the A allele of G27014A.

The nucleic acid sample typically comprises DNA or RNA. The presence of the at least one polymorphism in the nucleic acid sample can be detected by any of the variety of methods known in the art. For example, the at least one polymorphism can be detected by sequencing, e.g., sequencing of the region of the FRZB gene including the polymorphic site(s). The region of FRZB is optionally amplified prior to the sequencing step. As another example, the at least one polymorphism is detected by amplification, e.g., of the region of the FRZB gene including the polymorphic site(s). The amplification can be, e.g., an allele-specific amplification. The amplification can comprise a polymerase chain reaction (e.g., kinetic PCR), a ligase chain reaction, or the like. As yet another example, the polymorphism can be detected by hybridization of a nucleic acid probe. Thus, in one class of embodiments, to detect the polymorphism the nucleic acid sample is contacted with at least one sequence-specific oligonucleotide under conditions (e.g., stringent conditions) that allow binding of the at least one oligonucleotide to the nucleic acid sample. The at least one sequence-specific oligonucleotide hybridizes under stringent conditions to a region of the FRZB gene comprising the at least one osteoporosis-related polymorphism. Hybridization of the at least one oligonucleotide to the nucleic acid sample is then detected. In a related class of embodiments, the FRZB region comprising the polymorphism(s) is amplified prior to probe hybridization. Thus, in this class of embodiments, the nucleic acid sample is amplified to provide an amplified nucleic acid sample. The amplified nucleic acid sample is contacted with at least one sequence-specific oligonucleotide under conditions that allow binding of the oligonucleotide to the amplified nucleic acid sample (e.g., stringent conditions). The at least one sequence-specific oligonucleotide hybridizes under stringent conditions to a region of the FRZB gene comprising the at least one osteoporosis-related polymorphism. Hybridization of the at least one sequence-specific oligonucleotide to the amplified nucleic acid sample is detected. The presence of the at least one osteoporosis-related polymorphism can be, e.g., qualitatively or quantitatively detected.

In certain embodiments, the presence of the polymorphism inherited from one of the individual's parents provides an indication of the individual's risk for osteoporosis (e.g., when the associated FRZB allele exerts a dominant effect, such that inheritance of the polymorphism from one parent is sufficiently predictive). In other embodiments, the presence of the polymorphism inherited from both of the individual's parents provides an indication of the individual's risk for osteoporosis.

As noted, the methods are optionally combined with known clinical methods, e.g., to diagnose osteoporosis. Thus, the methods optionally include performing at least one clinical test for osteoporosis (e.g., a bone-turnover assay or a bone scan).

Yet another general class of embodiments provides methods for determining an individual's risk for obesity and/or osteoporosis. In the methods, the individual's genotype at one or more polymorphic sites in an FRZB gene is determined. A first genotype at the one or more polymorphic sites is statistically associated with an increased risk for obesity and/or osteoporosis as compared to a second genotype at the one or more polymorphic sites. Thus, for example, if the individual's genotype corresponds to the first genotype, the individual's risk for obesity and/or osteoporosis is greater than that of other individuals who have the second genotype.

Each polymorphic site can comprise one or more nucleotides. In a preferred class of embodiments, at least one of the one or more polymorphic sites consists of a single nucleotide position (i.e., the individual is genotyped for one or more SNPs, e.g., a plurality and/or a haplotype of SNPs). In certain embodiments, a plurality of the polymorphic sites each consists of a single nucleotide position (e.g., position 2628, 18679, 19524, 19575, 22242, 23043, 23415, 23549, 24791, 26794, or 27014 of SEQ ID NO:1). For example, at least one of the one or more polymorphic sites can be selected from the group consisting of: nucleotide position 2628, nucleotide position 18679, nucleotide position 19524, nucleotide position 22242, nucleotide position 24791, nucleotide position 26794, and nucleotide position 27014 of SEQ ID NO:1.

In some embodiments, the presence of a single allele of a particular polymorphism is sufficient to indicate whether the individual's risk of obesity and/or osteoporosis is increased or decreased. In other embodiments, two copies of an allele of a particular polymorphism must be present to indicate an increased or decreased risk of obesity and/or polymorphism (e.g., when the effect is recessive such that both homologous chromosomes must carry the allele). Thus, in one class of embodiments, the first genotype is statistically associated with an increased risk for obesity as compared to the second genotype. In one class of example embodiments, the first genotype comprises two T alleles and the second genotype two C alleles or one T allele and one C allele of T2303723C; the first genotype comprises two T alleles and the second genotype two C alleles or one T allele and one C allele of SNP C18679T; the first genotype comprises two A alleles and the second genotype two G alleles or one A allele and one G allele of SNP G19524A; the first genotype comprises two A alleles and the second genotype two T alleles or one A allele and one T allele of SNP T22242A; and/or the first genotype comprises two G alleles and the second genotype two A alleles or one G allele and one A allele of SNP A24791G. In a related class of embodiments, the first genotype is statistically associated with an increased risk for osteoporosis as compared to the second genotype. The first genotype comprises two C alleles and the second genotype two T alleles or one T allele and one C allele of SNP C18679T; the first genotype comprises two G alleles and the second genotype two A alleles or one A allele and one G allele of SNP G19524A; the first genotype comprises two A alleles and the second genotype two G alleles or one G allele and one A allele of SNP A24791G; the first genotype comprises two C alleles and the second genotype two G alleles or one C allele and one G allele of SNP C26794G; and/or the first genotype comprises two G alleles and the second genotype two A alleles or one G allele and one A allele of SNP G27014A.

Determining the individual's genotype typically involves obtaining a nucleic acid sample from the individual. Determining the individual's genotype can involve amplifying at least a portion of the FRZB gene from the nucleic acid sample, the portion comprising at least one of the one or more polymorphic sites. Such amplification can be, e.g., to directly determine the genotype or to facilitate detection of one or more polymorphisms by an additional step. In one class of embodiments, the individual's genotype is determined by performing an allele-specific amplification or an allele-specific extension reaction. In another class of embodiments, the individual's genotype is determined by sequencing at least a portion of the FRZB gene from the nucleic acid sample, the portion comprising at least one of the one or more polymorphic sites. In yet another class of embodiments, the individual's genotype is determined by hybridization of a nucleic acid probe, optionally after amplification of at least a portion of the FRZB gene. In one class of example embodiments, at least one of the one or more polymorphic sites consists of a single nucleotide position. In these embodiments, the nucleic acid sample is contacted with at least one sequence-specific oligonucleotide under stringent conditions. The oligonucleotide hybridizes under the stringent conditions to the nucleic acid sample when a first nucleotide occupies the nucleotide position defining the polymorphic site but not when a second nucleotide occupies the nucleotide position. Hybridization of the oligonucleotide to the nucleic acid sample is detected.

One aspect of the invention provides kits for detecting presence of a first predisposing or protective polymorphism in an FRZB gene, e.g., in a nucleic acid sample of an individual whose risk for osteoporosis and/or obesity is being assessed. Thus, one general class of embodiments provides a kit including one or more first oligonucleotides capable of detecting the first polymorphism and instructions for detecting the first polymorphism with the one or more first oligonucleotides and for correlating said detection to the individual's risk for osteoporosis and/or obesity, packaged in one or more containers.

Essentially all of the features noted for the method embodiments above apply to this embodiment as well, as relevant. For example, in a preferred class of embodiments, the first polymorphism is a single nucleotide polymorphism, e.g., a SNP selected from the group consisting of: the T allele of T2303723C, the C allele of T2303723C, the C allele of C18679T, the T allele of C18679T, the G allele of G19524A, the A allele of G19524A, the T allele of T22242A, the A allele of T22242A, the A allele of A24791G, the G allele of A24791G, the C allele of C26794G, the G allele of C26794G, the G allele of G27014A, and the A allele of G27014A. Other potential SNPs include, but are not limited to, either allele of T19575G, G23043A, G23415A, and T23549C.

In one aspect, the kit can be used to detect the presence of the first polymorphism by hybridization of a nucleic acid probe to the polymorphism. Thus, in one class of embodiments, the one or more first oligonucleotides comprise at least one probe. In certain embodiments, the first oligonucleotide hybridizes under stringent conditions to a region of the FRZB gene comprising the first polymorphism. In one class of embodiments, the first polymorphism is a first single nucleotide polymorphism comprising a first nucleotide at a first nucleotide position. In this class of embodiments, under stringent conditions, the first oligonucleotide hybridizes to a region of the FRZB gene comprising the first single nucleotide polymorphism with a signal to noise ratio that is at least 2× (e.g., at least 5× or at least 10×) the signal to noise ratio at which the first oligonucleotide hybridizes to the region of the FRZB gene comprising a second nucleotide at the first nucleotide position. The first oligonucleotide is typically fully complementary to the region of the FRZB gene comprising the first polymorphism, and typically comprises at least about 10 contiguous nucleotides complementary to the FRZB gene.

To facilitate detection of the polymorphism (e.g., through detection of hybridization between the one or more first oligonucleotides and a nucleic acid comprising the polymorphism), for example, the one or more first oligonucleotides optionally comprise a label, e.g., an isotopic, fluorescent, fluorogenic, luminescent or colorimetric label. In some embodiments, the label itself directly produces a detectable signal (e.g., a fluorescent label). In other embodiments, the kit also includes a reagent that detects the label (e.g., an enzyme that cleaves a colorimetric label, a binding moiety, or the like).

In one aspect, the one or more first oligonucleotides comprise one or more primers. The primer(s) can be used to detect the polymorphism, e.g., in an allele-specific amplification or extension reaction. For example, in one class of embodiments, the first polymorphism is a first single nucleotide polymorphism comprising a first nucleotide at a first nucleotide position, and the 3' nucleotide of one of the one or more first oligonucleotides is complementary to the first nucleotide.

The primer(s) can be used to amplify a region of FRZB comprising the polymorphism, e.g., for subsequent detection of the polymorphism by hybridization, sequencing, or the like. In one class of embodiments, the one or more first oligonucleotides comprise amplification primers, wherein the amplification primers amplify a nucleic acid sequence comprising the first polymorphism. In a related class of embodiments, the one or more first oligonucleotides comprise sequencing primers that flank the first polymorphism.

The one or more first oligonucleotides are optionally immobilized on a substrate. The substrate can be, for example, a planar substrate or a beaded substrate. The oligonucleotide(s) can be arranged in an array of other oligonucleotides used to detect other polymorphisms, e.g., other polymorphisms in FRZB.

The kit can optionally be used to detect more than one polymorphism (simultaneously or sequentially). Thus, in one class of embodiments, the kit also includes one or more second oligonucleotides capable of detecting a second polymorphism (and optionally third, fourth, fifth, etc. oligonucleotides capable of detecting third, fourth, fifth, etc. polymorphisms). The second polymorphism can be at the same polymorphic site as the first or at a different polymorphic site (in FRZB or a different gene), and can be protective or predisposing.

One general class of embodiments provides arrays for detecting presence of one or more predisposing and/or protective polymorphisms in an FRZB gene, e.g., in a nucleic acid sample of an individual whose risk for osteoporosis and/or obesity is being assessed. In one class of embodiments, the array comprises a substrate and a plurality of oligonucleotides, each of which oligonucleotides hybridizes to a region of the FRZB gene comprising at least one of the polymorphisms. The hybridization detects the presence of the polymorphism, and this detection provides an indication of the individual's risk for osteoporosis and/or obesity. The plurality of oligonucleotides are immobilized on the substrate. Typically, the array is used for detecting the presence of a plurality of polymorphisms, e.g., multiple alleles at a single polymorphic site and/or different polymorphic sites.

Essentially all of the features noted for the method and kit embodiments above apply to this embodiment as well, as relevant. For example, the one or more polymorphisms preferably comprise one or more single nucleotide polymorphisms. For example, at least one of the one or more polymorphisms can be selected from the group consisting of: the T allele of T2303723C, the C allele of T2303723C, the C allele of C18679T, the T allele of C18679T, the G allele of G19524A, the A allele of G19524A, the T allele of T22242A, the A allele of T22242A, the A allele of A24791G, the G allele of A24791G, the C allele of C26794G, the G allele of C26794G, the G allele of G27014A, and the A allele of G27014A. Other potential SNPs include, but are not limited to, either allele of T19575G, G23043A, G23415A, and T23549C.

In one class of embodiments in which the array can be used to detect presence of one or more SNPs, each of the oligonucleotides in the array hybridizes under stringent conditions to a region of the FRZB gene comprising one of the single nucleotide polymorphisms with a signal to noise ratio that is at least 2× (e.g., at least 5× or at least 10×) that at which the oligonucleotide hybridizes to a region of the FRZB gene comprising any of the remaining single nucleotide polymorphisms. Typically, one oligonucleotide is used to detect one SNP; that is, each of the oligonucleotides typically hybridizes to a distinct single nucleotide polymorphism.

As noted, the plurality of oligonucleotides are immobilized on a substrate, e.g., a planar substrate, a membrane, a glass slide, or the like. Typically, each of the plurality of oligonucleotides is immobilized at a known, pre-determined position on the substrate.

To facilitate detection of polymorphisms by specific hybridization with the oligonucleotides, each of the plurality of oligonucleotides is typically fully complementary to a region of the FRZB gene comprising one of the polymorphisms, and each of the plurality of oligonucleotides typically comprises at least about 10 contiguous nucleotides complementary to the FRZB gene. Each of the plurality of oligonucleotides optionally comprises a label, e.g., a label that facilitates detection of hybridization between the oligonucleotide and the corresponding polymorphism.

The array is optionally part of a system. Thus, one class of embodiments provides a system comprising an array of the invention and system instructions that correlate the detection of the presence of one or more predisposing or protective polymorphisms to the individual's risk for osteoporosis and/or obesity.

BRIEF DESCRIPTION OF THE DRAWINGS

FIG. 1 depicts exemplary FRZB SNPs. Nine base pairs centered on each SNP are shown; the upper strand corresponds to the strand whose sequence is listed in SEQ ID NO:1. SNP alleles illustrated are: C allele of C8679T (Panel A), T allele of C18679T (Panel B), G allele of G19524A (Panel C), A allele of G19524A (Panel D), T allele of T19575G (Panel E), G allele of T19575G (Panel F), T allele of T22242A (Panel G), A allele of T22242A (Panel H), G allele of G23043A (Panel I), A allele of G23043A (Panel J), G allele of G23415A (Panel K), A allele of G23415A (Panel L), T allele of T23549C (Panel M), C allele of T23549C (Panel N), A allele of A24791G (Panel 0), G allele of A24791G (Panel P), C allele of C26794G (Panel Q), G allele of C26794G (Panel R), G allele of G27014A (Panel S), A allele of G27014A (Panel T), T allele of T2303723C (Panel U), and C allele of T2303723C (Panel V).

DEFINITIONS

Before describing the invention in detail, it is to be understood that this invention is not limited to particular devices or biological systems, which can, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the invention, the preferred materials and methods are described herein. In describing and claiming the invention, the following terminology will be used in accordance with the definitions set out below.

As used in this specification and the appended claims, the singular forms "a", "an" and "the" include plural referents unless the content clearly dictates otherwise. Thus, for example, reference to "a cell" includes a combination of two or more cells; reference to "bacteria" includes mixtures of bacteria, and the like.

As used herein, the terms "nucleic acid," "polynucleotide" and "oligonucleotide" refer to single-stranded or double-stranded nucleotide polymers comprised of more than two nucleotide subunits covalently joined together. The nucleotides may comprise deoxyribonucleotides (containing 2-deoxy-D-ribose), ribonucleotides (containing D-ribose), and/or any other N-glycoside of a purine or pyrimidine base, or modified purine or pyrimidine bases, or any combination thereof. The sugar groups of the nucleotide subunits may also comprise modified derivatives of ribose or deoxyribose, such as O-methyl ribose. The nucleotide subunits of an oligonucleotide may be joined by phosphodiester linkages, phosphorothioate linkages, methyl phosphonate linkages or by other linkages, including, but not limited to, rare or non-naturally-occurring linkages, that do not prevent hybridization of the oligonucleotide. Furthermore, an oligonucleotide may have uncommon nucleotides or non-nucleotide moieties. With the addition of such analogs as locked nucleic acids (LNAs), the size of primers and probes can be reduced to as little as 8 nucleic acids. Locked nucleic acids are a novel class of bicyclic DNA analogs in which the 2' and 4' positions in the furanose ring are joined via an O-methylene (oxy-LNA), S-methylene (thio-LNA), or amino methylene (amino-LNA) moiety.

Oligonucleotide probes and amplification oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As used herein, an oligonucleotide does not consist of wild-type chromosomal DNA or the in vivo transcription products thereof.

Oligonucleotides which are primer and/or probe sequences, as described below, may comprise DNA, RNA or nucleic acid analogs such as uncharged nucleic acid analogs including, but not limited to, peptide nucleic acids (PNAs), which are disclosed in International Patent Application WO 92/20702, or morpholino analogs, which are described in U.S. Pat. Nos. 5,185,444, 5,034,506, and 5,142,047, all of which are herein incorporated by reference in their entireties. Such sequences can routinely be synthesized using a variety of techniques currently available. For example, a sequence of DNA can be synthesized using conventional nucleotide phosphoramidite chemistry and the instruments available from Applied Biosystems, Inc. (Foster City, Calif.); DuPont (Wilmington, Del.); or Milligen (Bedford, Mass.). Similarly, and when desirable, the sequences can be labeled using methodologies well known in the art such as described in U.S. Pat. Nos. 5,464,746; 5,424,414; and 4,948,882, all of which are herein incorporated by reference in their entireties. Oligonucleotides (including, e.g., labeled or modified oligos) can also be ordered from a variety of commercial sources known to persons of skill. Essentially any nucleic acid can be custom ordered from any of a variety of commercial sources, for example, The Midland Certified Reagent Company, The Great American Gene Company, ExpressGen Inc., and QIAGEN, among many others.

A nucleic acid, nucleotide, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, $N^6$-methyl-adenine, $N^6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-iso-pentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611, 5,955,589, 5,844,106, 5,789,562, 5,750,343, 5,728,525, and 5,679,785, each of which is incorporated herein by reference in its entirety.

Furthermore, a nucleic acid, nucleotide, polynucleotide or oligonucleotide can comprise one or more modified sugar moieties including, but not limited to, arabinose, 2-fluoroarabinose, xylulose, and hexose. A nucleic acid, nucleotide, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

An "isolated" nucleic acid molecule, as used herein, is one that is separated from nucleotide sequences which normally flank the nucleic acid molecule and/or has been completely or partially purified from other biological material (e.g., protein) normally associated with the nucleic acid.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the invention. An isolated nucleic acid molecule or nucleotide sequence can include a nucleic acid molecule or nucleotide sequence that is synthesized chemically or by recombinant means. Also, isolated polynucleotides include recombinant DNA molecules in heterologous organisms, as well as partially or substantially purified DNA molecules in solution. In vivo and in vitro RNA transcripts of the DNA molecules of the invention are also encompassed by "isolated" nucleotide sequences. Such polynucleotides are useful, e.g., as primers and/or probes for detecting polymorphisms, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis.

The isolated nucleic acid molecules may be RNA, mRNA, DNA, or cDNA, for example, and may be double- or single-stranded. They may encode the sense strand, the non-coding regions, and/or the antisense strand. The nucleic acid/molecule can include all or a portion of the coding sequence of the gene and can further comprise additional non-coding regions such as introns and non-coding 3' and 5' sequences (including regulatory sequences, for example). Additionally, the nucleic acid molecule can be fused to a marker sequence, for example, a sequence that can be used to purify the nucleic acid molecule.

The nucleic acid molecules of the invention can comprise one or more modified nucleotide residues. The modification may be at the base, sugar and/or phosphate moiety and include, for example, halogenation, hydroxylation, alkylation, an attached linker and/or label. The modifications can further comprise, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequence via hydrogen bonding and other chemical interactions. Such molecules include, for example, those in which peptide linkages substitute for phosphate linkages in the backbone of the molecule.

In certain embodiments, nucleic acid molecules of the invention include, but are not limited to, FRZB mRNA, cDNA and/or genomic DNA molecules. Nucleic acid molecules of the invention also include oligonucleotides, e.g., an oligonucleotide comprising one or more of the FRZB SNPs described herein.

As used herein, the term "primer" refers to an oligonucleotide having a hybridization specificity sufficient for the initiation of an enzymatic polymerization under predetermined conditions, for example in an amplification technique such as polymerase chain reaction (PCR), in a process of sequencing, in a method of reverse transcription and/or the like.

As used herein, the term "probe" refers to an oligonucleotide having a hybridization specificity sufficient for binding to a defined target sequence under predetermined conditions, for example in an amplification technique such as a 5'-nuclease reaction, in a hybridization-dependent detection method, such as a Southern or Northern blot, and/or the like. Primers and probes may be used in a variety of ways and may be defined by the specific use. For example, a "capture probe" is immobilized or can be immobilized on a solid support by any appropriate means, including, but not limited to: by covalent bonding, by adsorption, by hydrophobic and/or electrostatic interaction, or by direct synthesis on a solid support (see in particular patent application WO 92 10092). A "detection probe" may be labeled by means of a marker chosen, for example, from radioactive isotopes, enzymes, in particular enzymes capable of acting on a chromogenic, fluorescent or luminescent substrate (in particular a peroxidase or an alkaline phosphatase), chromophoric chemical compounds, chromogenic, fluorigenic or luminescent compounds, analogues of nucleotide bases, and ligands such as biotin. Illustrative fluorescent compounds include, for example, fluorescein, carboxyfluorescein, tetrachlorofluorescein, hexachlorofluorescein, Cy3, tetramethylrhodamine, Cy3.5, carboxy-x-rhodamine, Texas Red, Cy5, and Cy5.5. Illustrative luminescent compounds include, for example, luciferin and 2,3-dihydrophthalazinediones, such as luminol.

All of the oligonucleotides, primers and probes of the invention, whether hybridization assay probes, amplification primers, or other oligonucleotides, may be modified with chemical groups to enhance their performance or to facilitate the characterization of amplification products. For example, backbone-modified oligonucleotides such as those having phosphorothioate or methylphosphonate groups which render the oligonucleotides resistant to the nucleolytic activity of certain polymerases or to nuclease enzymes may allow the use of such enzymes in an amplification or other reaction. Another example of modification involves using non-nucleotide linkers (e.g., Arnold, et al., "Non-Nucleotide Linking Reagents for Nucleotide Probes", EP 0 313 219 hereby incorporated by reference herein in its entirety) incorporated between nucleotides in the nucleic acid chain which do not interfere with hybridization or the elongation of the primer. Amplification oligonucleotides may also contain mixtures of the desired modified and natural nucleotides.

The 3' end of an amplification primer or a probe may optionally be blocked to prevent initiation of DNA synthesis as described by McDonough, et al., entitled "Nucleic Acid Sequence Amplification", WO94/03472 which enjoys common ownership with the invention and is hereby incorporated by reference herein in its entirety. A mixture of different 3' blocked amplification oligonucleotides, or of 3' blocked and unblocked oligonucleotides, may increase the efficiency of nucleic acid amplification, as described therein. The 5' end of the oligonucleotides may be modified to be resistant to the 5'-exonuclease activity present in some nucleic acid polymerases. Such modifications can be carried out by adding a non-nucleotide group to the terminal 5' nucleotide of the primer using techniques such as those described by Arnold, et al., supra, entitled "Non-Nucleotide Linking Reagents for Nucleotide Probes", incorporated by reference herein.

Once synthesized, selected oligonucleotide probes may be labeled by any of several well-known methods (e.g., J. Sambrook, infra). Useful labels include radioisotopes as well as non-radioactive reporting groups. Isotopic labels include $^3$H, $^{35}$S, $^{32}$P, $^{125}$I, $^{57}$Co and $^{14}$C. Isotopic labels can be introduced into the oligonucleotide by techniques known in the art such as nick translation, end labeling, second strand synthesis, the use of reverse transcription, and by chemical methods. When using radiolabeled probes hybridization can be detected, e.g., by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as described by Arnold, et al., supra "Non-Nucleotide Linking Reagents for Nucleotide Probes," incorporated by reference herein. Non-isotopic labels include fluorescent molecules; chemiluminescent molecules, enzymes, cofactors, enzyme substrates, haptens or other ligands.

In one embodiment, the probes are labeled with an acridinium ester. Acridinium ester labeling may be performed as described by Arnold et al., U.S. Pat. No. 5,185,439, entitled "Acridinium Ester Labeling and Purification of Nucleotide Probes," issued Feb. 9, 1993 and hereby incorporated by reference herein in its entirety.

The term "sequence-specific oligonucleotide" refers to an oligonucleotide that hybridizes (under defined conditions) to a target nucleic acid with a signal to noise ratio at least 2× higher than a signal to noise ratio at which it hybridizes to a nucleic acid that is not the target. For example, a sequence-specific oligonucleotide can hybridize, under stringent conditions, to a region of FRZB comprising a first allele of a SNP (the target nucleic acid) with a signal to noise ratio at least 2× (e.g., at least 5× or 10×) higher than a signal to noise ratio at which the oligonucleotide hybridizes to the region of FRZB comprising a second allele of the SNP.

The term "FRZB gene" or "FRZB locus" refers to the genomic nucleic acid sequence that encodes the FRZB protein. The nucleotide sequence of a gene, as used herein, encompasses coding regions, referred to as exons, intervening, non-coding regions, referred to as introns, and upstream and/or downstream regions. Upstream or downstream regions can include regions of the gene that are transcribed but not part of an intron or exon, or regions of the gene that comprise, for example, binding sites for factors that modulate gene transcription. The sequence for the human FRZB genomic sequence is provided at GenBank accession numbers NT_005100.3, NT_005265, and NT_005403, and a portion of the sequence is provided herein as SEQ ID NO:1. The sequence for the human FRZB mRNA is provided at GenBank accession number NM_001463, and is provided herein as SEQ ID NO:2.

The term "allele", as used herein, refers to a sequence variant of a gene and/or a polymorphism. Alleles are typically identified with respect to one or more polymorphic positions, with the rest of the gene sequence unspecified. For example, a FRZB allele may be defined by the nucleotide present at a single SNP, or by the nucleotides present at a plurality of SNPs. Examples of such FRZB SNPs are provided in Table 1, below.

For convenience, the allele present at the higher or highest frequency in the population will be referred to as the wild-type allele, and less frequent allele(s) will be referred to as mutant allele(s). (However, it is worth noting that an allele which is more frequent in one population may be less frequent in a different population.) This designation of an allele as a mutant is meant solely to distinguish the allele from the wild-type allele and is not meant to indicate a change or loss of function.

The terms "polymorphic" and "polymorphism", as used herein, refer to the condition in which two or more variants of a specific genomic sequence, or the encoded amino acid sequence, can be found in a population. The terms refer either to the nucleic acid sequence or the encoded amino acid sequence; the use will be clear from the context. The term "polymorphic region" or "polymorphic site" refers to a region of the nucleic acid where the nucleotide difference that distinguishes the variants occurs, or, for amino acid sequences, a region of the amino acid sequence where the amino acid difference that distinguishes the protein variants occurs. As used herein, the term "single nucleotide polymorphism", or SNP, refers to polymorphism at a polymorphic site consisting of a single nucleotide position. As will be clear from the context, the term polymorphism can refer to a specific variant sequence at a polymorphic site; for example, the term SNP can refer to the specific nucleotide (e.g., A, C, G, or T) occupying a polymorphic site consisting of a single nucleotide position.

Individual amino acids in a sequence are represented herein as AN or NA, wherein A is the amino acid in the sequence and N is the position in the sequence. In the case that position N is polymorphic, it is convenient to designate one variant (e.g., the more frequent variant) as $A_1N$ and the other variant (e.g., the less frequent variant) as $NA_2$. Alternatively, the polymorphic site, N, is represented as $A_1NA_2$, wherein $A_1$ is the amino acid in one variant and $A_2$ is the amino acid in the other variant. It is worth noting that an allele which is more frequent in one population may be less frequent in a different population. Either the one-letter or three-letter codes are used for designating amino acids (see Lehninger, *BioChemistry 2nd ed.*, 1975, Worth Publishers, Inc. New York, N.Y.: pages 73-75, incorporated herein by reference). The amino acid positions are numbered based on the sequence of the mature FRZB protein.

Representations of nucleotides and single nucleotide variations in DNA sequences are analogous to the representations of amino acids. For example, C18679T represents a single nucleotide polymorphism at nucleotide position 18679, wherein cytosine is present in the more frequent (wild-type) allele in the population and thymidine is present in the less frequent (mutant) allele. In general, a SNP can be represented as $A_1NA_2$, wherein $A_1$ is the nucleotide present in one variant and $A_2$ is the nucleotide in the other variant. The single letter codes for the nucleotides are well known to those in the art, i.e., C for cytosine; A for adenine; T for thymidine, G for guanine, I for inosine, and U for uracil. It will be clear that in a double stranded form, the complementary strand of each allele will contain the complementary base at the polymorphic position; a SNP (or other polymorphism) can thus be described and/or detected with reference to the nucleotide(s) occupying the polymorphic site on either strand.

As used herein, the term "predisposing polymorphism" refers to a polymorphism that is positively associated with a condition, such as, for example, obesity and/or osteoporosis. The presence of a predisposing polymorphism in an individual could be indicative that the individual has an increased risk for the disease relative to an individual without the polymorphism. The term "protective polymorphism" refers to a polymorphism that is negatively associated with a condition. The presence of a protective polymorphism in an individual could be indicative that the individual has a decreased risk for the disease relative to an individual without the polymorphism.

The term "obesity-associated polymorphism" or "obesity-related polymorphism" refers to a polymorphism that is associated with obesity (e.g., with a high body mass index), either positively or negatively.

The term "osteoporosis-associated polymorphism" or "osteoporosis-related polymorphism" refers to a polymorphism that is associated with osteoporosis (e.g., with increased incidence of hip and/or vertebral fracture and/or decreased bone mineral density), either positively or negatively.

The term "association" or "associated with" in the context of this invention refers to the presence of a disease or phenotypic trait in individuals with one or more specific alleles or polymorphisms in one or more specific genes.

As used herein, the term "odds ratio" (OR) refers to the ratio of the frequency of the disease in individuals having a particular marker (allele or polymorphism) to the frequency of the disease in individuals without the marker (allele or polymorphism).

As used herein, the term "linkage disequilibrium" (LD) refers to alleles at different loci that are not associated at random, i.e., not associated in proportion to their frequencies. If the alleles are in positive linkage disequilibrium, then the alleles occur together more often than expected, assuming statistical independence. Conversely, if the alleles are in negative linkage disequilibrium, then the alleles occur together less often than expected assuming statistical independence.

The term "genotype", as used herein, refers to a description of the allele(s) of a gene or genes contained in an individual or a sample. As used herein, no distinction is made between the genotype of an individual and the genotype of a sample originating from the individual. Although, typically, a genotype is determined from samples of diploid cells, a genotype can be determined from a sample of haploid cells, such as a sperm cell. Similarly, an individual's "genotype at one or more polymorphic sites" refers to a description of the allele(s) of one or more polymorphisms contained in the individual or a sample. For example, an individual's genotype for a SNP is defined by the nucleotide present at that polymorphic site.

The term "haplotype", as used herein, refers to a description of the variants of a gene or genes contained on a single chromosome, i.e., the genotype of a single chromosome. A haplotype is a set of maternally inherited alleles, or a set of paternally inherited alleles, at any locus. A haplotype may also refer to two or more SNPs grouped together.

As used herein, the term "target region" refers to a region of a nucleic acid which is to be analyzed and usually includes at least one polymorphic region.

The term "stringent" as used herein refers to hybridization and wash conditions that are at or near the Tm for a particular sequence, taking into account considerations such as salt concentration and oligonucleotide length and base composition, for example. Generally, stringent conditions are selected to be about 5° C. to 15° C. lower than the thermal melting point (Tm) for the specific sequence at a defined ionic strength and pH. Higher stringency conditions are optionally selected, for example, equal to the Tm or even 5° C. or more greater than the Tm. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 50° C. for a sequence with a Tm of about 55-65° C. As other factors may significantly affect the stringency of hybridization, including, among others, base composition, length of the nucleic acid strands, the presence of organic solvents, and the extent of base mismatching, the combination of parameters is more important than the absolute measure of any one.

A "label" is a moiety that facilitates detection of a molecule. Common labels in the context of the present invention include fluorescent, luminescent, and/or colorimetric labels. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "polynucleotide sequence", "nucleotide sequence", or "nucleic acid sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

A variety of additional terms are defined or otherwise characterized herein.

DETAILED DESCRIPTION

Certain embodiments of the invention stem from the observation that at least one polymorphism in the FRZB gene is correlated with an individual's risk for obesity and/or osteoporosis. Further embodiments provide methods for detecting an individual's increased or decreased risk for obesity and/or osteoporosis. Further embodiments provide kits, reagents and arrays useful for detecting an individual's risk for obesity and/or osteoporosis.

In one aspect, the invention provides a method for detecting an individual's increased or decreased risk for obesity by detecting the presence of at least one obesity-associated polymorphism in the FRZB locus in a nucleic acid sample of the individual, wherein the presence of said at least one polymorphism indicates the individual's increased or decreased risk for obesity.

In a further aspect, the invention provides a method for detecting an individual's increased or decreased risk for osteoporosis by detecting the presence of at least one osteoporosis-associated polymorphism in the FRZB locus in a nucleic acid sample of the individual, wherein the presence of said at least one polymorphism indicates the individual's increased or decreased risk for osteoporosis.

In a further embodiment, the invention provides a method for detecting the presence of osteoporosis in an individual by a combination of the diagnostic test for predisposition and at least one other clinical test for osteoporosis, including but not limited to: a bone-turnover assay and any type of bone scan. Other diseases, conditions or criteria which may predispose for or be used in addition to the above include, but are not limited to, hyperthyroidism, posttransplantation, maladsorption, hyperparathyroidism, alcoholism, and family history.

In one embodiment, the FRZB polymorphism is selected from the FRZB polymorphisms listed in Table 1. In a further embodiment, more than one polymorphism is detected in the nucleic acid sample, at least one of which is selected from the polymorphisms listed in Table 1. In a further embodiment, at least two of the polymorphisms selected from those listed in Table 1 are detected. Examples of polymorphisms in FRZB that can be used include but are not limited to: T2303723C, C18679T, G19524A, T19575G, T22242A, G23043A, G23415A, T23549C, A24791G, C26794G, and G27014A.

The individual can be any mammal, including human, and belong to any race or population. The individual may be male or female. However, it is understood that the methods, kits and compositions described herein would be ideally suited for the analysis of osteoporosis in women over age 50, and/or post-menopausal women. Further, the methods, kits and compositions described herein would be ideally suited to the analysis of osteoporosis in men or women between the ages of 35 and 77. More particularly, men and women over 40 years of age would be ideally suited for analysis.

In a further embodiment, men and women between birth and the age of about 75 may be screened for a predisposition to obesity, more specifically, men and women between the ages of 5 and 55. Of interest would be to identify an individual predisposed to obesity at an early age and/or prenatally, in order to prevent the weight gain before it happens. In a further embodiment, the individual is identified at certain high-risk times or situations in the lifetime. Such times include but are not limited to: adolescence, menopause, old age, periods of depression, illnesses which predispose to obesity and/or radical life changes. In addition, before starting on a diet regimen, it may be of interest to determine a patient's predisposition to obesity, which may influence the type of program selected, speed of weight loss, and the ability of the patient to maintain a different weight level.

The nucleic acid sample can be obtained from any part of the individual's body, including, but not limited to: hair, skin, nails, tissues, such as organs or tumors, or bodily fluids, such as saliva, blood, plasma, serum, spinal fluid, lymph, synovial fluid, semen, seminal fluid, bronchio-alveolar lavage, urine, or tears, as well as samples of isolated blood or tissue cells or in vitro cell culture constituents (including, but not limited to, conditioned medium obtained from the growth of cells in cell culture medium, recombinant cells and cell components). The nucleic acid sample can, but need not, be amplified by any amplification method including, but not limited to, polymerase chain reaction ("PCR").

The polymorphism can be any predisposing or protective polymorphism in the FRZB locus. In one embodiment of the invention, the polymorphism can be any polymorphism identified as predisposing or protective by methods taught herein. In one embodiment, the polymorphism can be a single nucleotide polymorphism (SNP) in the FRZB locus. In another embodiment, specific haplotypes in the FRZB locus as well as specific combinations of, and interactions between, SNPs at this locus can be indicative of an increased or a decreased risk of obesity and/or osteoporosis.

In a further embodiment, the presence of the polymorphism from only one parent is sufficiently predictive. In a further embodiment, the presence of the polymorphism from both parents is sufficiently predictive.

The polymorphism can be detected by any method known in the art for detecting the presence of a specific polymorphism in a nucleic acid sample. These methods include, but are not limited to, contacting the nucleic acid sample with one or more nucleic acid molecules that hybridize under stringent hybridization conditions to at least one FRZB polymorphism and detecting the hybridization, detection by amplification of the nucleic acid sample by, for example, PCR, and by direct sequencing of the nucleic acid sample.

In certain embodiments, an individual's risk for osteoporotic or obesity-related diseases is diagnosed from the individual's FRZB genotype. An individual who has at least one polymorphism statistically associated with osteoporosis and/or obesity possesses a factor contributing to either an increased or a decreased risk as compared to an individual without the polymorphism. The statistical association of various FRZB polymorphism (sequence variants) with obesity and/or osteoporosis is shown in the examples.

The genotype can be determined using any method capable of identifying nucleotide variation, e.g., nucleotide variation consisting of single nucleotide polymorphic sites. The particular method used is not a critical aspect of the invention. A number of suitable methods are described below.

In one embodiment of the invention, genotyping is carried out using oligonucleotide probes specific to variant FRZB sequences. In one embodiment, a region of the FRZB gene which encompasses one or several polymorphic sites of interest is amplified prior to, or concurrent with, the hybridization of probes directed to such sites. Probe-based assays for the detection of sequence variants are well known in the art.

Alternatively, genotyping is carried out using allele-specific amplification or extension reactions, wherein allele-specific primers are used which support primer extension only if the targeted allele is present. Typically, an allele-specific primer hybridizes to the FRZB gene such that the 3' terminal nucleotide aligns with a polymorphic position. Allele-specific amplification reactions and allele-specific extension reactions are well known in the art.

Another aspect of the invention relates to a kit useful for detecting the presence of a predisposing or a protective polymorphism in the FRZB locus in a nucleic acid sample of an individual whose risk for osteoporosis and/or obesity is being assessed. The kit can comprise one or more oligonucleotides capable of detecting a predisposing or protective polymorphism in the FRZB locus as well as instructions for using the kit to detect susceptibility to obesity and/or osteoporosis. In preferred embodiments, the oligonucleotide or oligonucleotides each individually comprise a sequence that hybridizes under stringent hybridization conditions to at least one FRZB polymorphism. In some embodiments, the oligonucleotide or oligonucleotides each individually comprise a sequence that is fully complementary to a nucleic acid sequence comprising a FRZB polymorphism.

In some embodiments, the oligonucleotide can be used to detect the presence of the FRZB polymorphism by hybridizing to the polymorphism under stringent hybridizing conditions. In some embodiments, the oligonucleotide can be used as an extension primer in either an amplification reaction such as PCR or a sequencing reaction, wherein FRZB polymorphism is detected either by amplification or sequencing.

In certain embodiments, the kit can further comprise amplification or sequencing primers which can, but need not, be sequence-specific. The kit can also comprise reagents for labeling one or more of the oligonucleotides, or comprise labeled oligonucleotides. Optionally, the kit can comprise reagents to detect the label.

In some embodiments, the kit can comprise one or more oligonucleotides that can be used to detect the presence of two or more predisposing or protective FRZB polymorphisms or combinations of predisposing polymorphisms, protective polymorphisms or both.

In another aspect, the invention provides an array useful for detecting the presence of a predisposing or a protective FRZB polymorphism in a nucleic acid sample of an individual whose risk for obesity and/or osteoporosis is being assessed. The array can comprise one or more oligonucleotides capable of detecting a predisposing or protective FRZB polymorphism. The oligonucleotides can be immobilized on a substrate, e.g., a membrane or glass. In preferred embodiments, the oligonucleotide or oligonucleotides each individually comprise a sequence that can hybridize under stringent hybridization conditions to a nucleic acid sequence comprising a FRZB polymorphism. In some embodiments, the oligonucleotide or oligonucleotides each individually comprise a sequence that is fully complementary to a nucleic acid sequence comprising a FRZB polymorphism. The oligonucleotide or oligonucleotides can, but need not, be labeled. In some embodiments, the array can be a microarray.

In some embodiments, the array can comprise one or more oligonucleotides used to detect the presence of two or more predisposing or protective FRZB polymorphisms or combinations of predisposing polymorphisms, protective polymorphisms or both.

One aspect of the invention provides nucleic acids, for example, nucleic acids comprising one or more novel polymorphisms in the FRZB gene and/or nucleic acids useful for detecting one or more FRZB polymorphisms. Accordingly, one embodiment of the invention is an isolated nucleic acid molecule comprising a portion of the FRZB gene, its complement, and/or a variant thereof. Preferably said variant comprises at least one of the polymorphisms identified herein. Even more preferably, said variant comprises at least one of the polymorphisms identified herein to be associated with obesity. Alternatively, said variant comprises at least one of the polymorphisms identified herein to be associated with osteoporosis. Thus, in one embodiment, the nucleic acid molecule comprises at least one of the FRZB polymorphisms provided in Table 1. In a further embodiment, the nucleic acid molecule comprises or consists of a primer and/or a probe specific to at least one of the polymorphisms identified in the FRZB gene (e.g., those identified herein to be associated with obesity and/or osteoporosis).

SNPS

In one aspect, the invention provides a method for detecting an individual's increased or decreased risk for obesity by detecting the presence of one or more FRZB SNPs in a nucleic acid sample of the individual, wherein the presence of said SNP(s) indicates the individual's increased or decreased risk for obesity. In a further aspect, the invention provides a method for detecting an individual's increased or decreased risk for osteoporosis by detecting the presence of one or more FRZB SNPs in a nucleic acid sample of the individual, wherein the presence of said SNP(s) indicates the individual's increased or decreased risk for osteoporosis. The SNPs can be any SNPs in the FRZB locus including SNPs in exons, introns and/or upstream and/or downstream regions; Examples of such SNPs include, but are not limited to, those provided in Table 1, below, and discussed in detail in the Examples. In one embodiment, the SNPs present in the FRZB locus are identified by genotyping the FRZB SNPs.

TABLE 1

FRZB SNPs

| FRZB SNP | Standard Name | Position in NT_005403 | SNP Source | Pos. in Gene/Change |
|---|---|---|---|---|
| FRZB1_T2303723C | NT_005265.11_2303723 | NT_005403_33933138 | rs6433992 | Intron 1/T-C |
| FRZB_C18679T | NT_005100.3_18679 | NT005403_33917116 | rs288330 | Intron 2/C-T |
| FRZB_G19524A | NT_005100.3_19524 | NT005403_33916271 | rs2242070 | Intron 3/G-A |
| FRZB_T19575G | NT_005100.3_19575 | NT005403_33916220 | RMS SNP | Intron 3/T-G |
| FRZB_T22242A | NT_005100.3_22242 | NT005403_33913553 | rs288327 | Intron 3/T-A |
| FRZB_G23043A | NT_005100.3_23043 | NT005403_33912752 | rs288326 | Exon 4/G-A-> Arg200Trp |
| FRZB_G23415A | NT_005100.3_23415 | NT005403_33912380 | rs1561369 | Intron 4/G-A |
| FRZB_T23549C | NT_005100.3_23549 | NT005403_33912246 | rs288325 | Intron 4/T-C |
| FRZB_A24791G | NT_005100.3_24791 | NT005403_33911004 | rs288324 | Intron 5/A-G |
| FRZB_C26794G | NT_005100.3_26794 | NT005403_33909000 | rs7775 | Exon 6/C-G-> Arg324Gly |
| FRZB_G27014A | NT_005100.3_27014 | NT005403_33908780 | rs13009 | 3' UTR/G-A |

In certain embodiments, the genotype of one FRZB SNP can be used to determine an individual's risk for obesity and/or osteoporotic disease. In other embodiments, the genotypes of a plurality of FRZB SNPs can be used. In other embodiments, certain combinations of SNPs at either the same or different loci can be used. It is to be understood that some of the SNPs related to an increased or decreased risk of obesity may be the same as those related to either an increased or decreased risk of osteoporosis.

Genotyping Methods

In the methods of the invention, the alleles present in a sample are identified by identifying the nucleotide present at one or more of the polymorphic sites in a nucleic acid sample of an individual. A number of methods are known in the art for identifying the nucleotide present at polymorphic sites. The particular method used to identify the genotype is not a critical aspect of the invention. Although considerations of performance, cost, and convenience will make particular methods more desirable than others, it will be clear that any method that can identify the nucleotide present will provide the information needed to identify the genotype. Preferred genotyping methods involve DNA sequencing, allele-specific amplification, or probe-based detection of amplified nucleic acid FRZB alleles can be identified by DNA sequencing methods, such as the chain termination method (Sanger et al., 1977, Proc. Natl. Acad. Sci., 74:5463-5467, incorporated herein by reference), which are well known in the art. In one embodiment, a portion of the gene encompassing the polymorphic site is amplified and either cloned into a suitable plasmid and then sequenced, or sequenced directly. PCR-based sequencing is described in U.S. Pat. No. 5,075,216; Brow, in PCR Protocols, 1990, (Innis et al., eds., Academic Press, San Diego), chapter 24; and Gyllensten, in PCR Technology, 1989 (Erlich, ed., Stockton Press, New York), chapter 5; each incorporated herein by reference. Typically, sequencing is performed using an automated DNA sequencer, which are commercially available from, for example, PE Biosystems (Foster City, Calif.), Pharmacia (Piscataway, N.J.), Genomyx Corp. (Poster City, Calif.), LI-COR Biotech (Lincoln, Nebr.), GeneSys technologies (Sauk City, Wis.), and Visible Genetics, Inc. (Toronto, Canada).

FRZB alleles can also be identified using amplification-based genotyping methods. Various nucleic acid amplification methods known in the art can be used in to detect nucleotide changes in a target nucleic acid. A preferred method is the polymerase chain reaction (PCR), which is now well known in the art, and described in U.S. Pat. Nos. 4,683,195; 4,683,202; and 4,965,188; each incorporated herein by reference. Examples of the numerous articles published describing methods and applications of PCR are found in PCR Applications, 1999, (Innis et al., eds., Academic Press, San Diego), PCR Strategies, 1995, (Innis et al., eds., Academic Press, San Diego); PCR Protocols, 1990, (Innis et al, eds., Academic Press, San Diego); and PCR Technology, 1989, (Erlich, ed., Stockton Press, New York); each incorporated herein by reference. Commercial vendors, such as PE Biosystems (Foster City, Calif.) market PCR reagents and publish PCR protocols.

Other suitable amplification methods include the ligase chain reaction (Wu and Wallace, 1988, *Genomics* 4:560-569); the strand displacement assay (Walker et al., 1992, *Proc. Natl. Acad. Sci. USA* 89:392-396, Walker et al. 1992, *Nucleic Acids Res.* 20:1691-1696, and U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., 1989, *Proc. Natl. Acad. Sci. USA,* 86:1173-1177); and self-sustained sequence replication (3SR) (Guatelli et al., 1990, *Proc. Natl. Acad. Sci. USA,* 87:1874-1878 and WO 92/08800); each incorporated herein by reference. Alternatively, methods that amplify the probe to detectable levels can be used, such as Qβ-replicase amplification (Kramer et al., 1989, *Nature,* 339:401-402, and Lomeli et al., 1989, *Clin. Chem.,* 35:1826-1831, both of which are incorporated herein by reference). A review of known amplification methods is provided in Abramson et al, 1993, *Current Opinion in Biotechnology,* 4:41-47, incorporated herein by reference.

Genotyping can also be carried out by detecting and analyzing FRZB mRNA under conditions when both maternal and paternal chromosomes are transcribed. Amplification of RNA can be carried out by first reverse-transcribing the target RNA using, for example, a viral reverse transcriptase, and then amplifying the resulting cDNA, or using a combined high-temperature reverse-transcription-polymerase chain reaction (RT-PCR), as described in U.S. Pat. Nos. 5,310,652; 5,322,770; 5,561,058; 5,641,864; and 5,693,517; each incorporated herein by reference (see also Myers and Sigua, 1995, in PCR Strategies, supra, chapter 5).

FRZB alleles can also be identified using allele-specific amplification or primer extension methods, which are based on the inhibitory effect of a terminal primer mismatch on the ability of a DNA polymerase to extend the primer. To detect an allele sequence using an allele-specific amplification or extension-based method, a primer complementary to the FRZB genes is chosen such that the 3' terminal nucleotide hybridizes at the polymorphic position. In the presence of the allele to be identified, the primer matches the target sequence at the 3' terminus and primer is extended. In the presence of only the other allele, the primer has a 3' mismatch relative to the target sequence and primer extension is either eliminated or significantly reduced. Allele-specific amplification- or extension-based methods are described in, for example, U.S. Pat. Nos. 5,137,806; 5,595,890; 5,639,611; and U.S. Pat. No. 4,851,331, each incorporated herein by reference.

Using allele-specific amplification-based genotyping, identification of the alleles requires only detection of the presence or absence of amplified target sequences. Methods for the detection of amplified target sequences are well known in the art. For example, gel electrophoresis (see Sambrook et al., 1989, infra) and the probe hybridization assays described above have been used widely to detect the presence of nucleic acids.

Allele-specific amplification-based methods of genotyping can facilitate the identification of haplotypes, as described in the examples. Essentially, the allele-specific amplification is used to amplify a region encompassing multiple polymorphic sites from only one of the two alleles in a heterozygous sample. The SNP variants present within the amplified sequence are then identified, such as by probe hybridization or sequencing.

An alternative probe-less method, referred to herein as a kinetic-PCR method, in which the generation of amplified nucleic acid is detected by monitoring the increase in the total amount of double-stranded DNA in the reaction mixture, is described in Higuchi et al., 1992, *Bio/Technology,* 10:413-417; Higuchi et al., 1993, *Bio/Technology,* 11:1026-1030; Higuchi and Watson, in PCR Applications, supra, Chapter 16; U.S. Pat. Nos. 5,994,056 and 6,171,785; and European Patent Publication Nos. 487,218 and 512,334, each incorporated herein by reference. The detection of double-stranded target DNA relies on the increased fluorescence that DNA-binding dyes, such as ethidium bromide or SYBR™ Green, exhibit when bound to double-stranded DNA. The increase of double-stranded DNA resulting from the synthesis of target sequences results in an increase in the amount of dye bound to double-stranded DNA and a concomitant detectable increase in fluorescence. For genotyping using the kinetic-PCR methods, amplification reactions are carried out using a pair of primers specific for one of the alleles, such that each amplification can indicate the presence of a particular allele. For example, by performing two amplifications, one using primers specific for the wild-type allele and one using primers specific for the mutant allele, the genotype of the sample with respect to that SNP can be determined. Similarly, by carrying out four amplifications, each with one of the possible pairs possible using allele specific primers for both the upstream and downstream primers, the genotype of the sample with respect to two SNPs can be determined. This gives haplotype information for a pair of SNPs.

Alleles can be also identified using probe-based methods, which rely on the difference in stability of hybridization duplexes formed between a probe and its corresponding target sequence comprising a FRZB allele. Under sufficiently stringent hybridization conditions, stable duplexes are formed only between a probe and its target allele sequence and not other allele sequences. The presence of stable hybridization duplexes can be detected by any of a number of well known methods. In general, it is preferable to amplify a nucleic acid encompassing a polymorphic site of interest prior to hybridization in order to facilitate detection. However, this is not necessary if sufficient nucleic acid can be obtained without amplification.

A probe suitable for use in the probe-based methods of the invention, which contains a hybridizing region either substantially complementary or exactly complementary to a target region of the FRZB gene or the complement thereof, wherein the target region encompasses the polymorphic site, and exactly complementary to one of the two allele sequences at the polymorphic site, can be selected using the guidance provided herein and well known in the art. Similarly, suitable hybridization conditions (e.g., stringent hybridization conditions), which depend on the exact size and sequence of the probe, can be selected empirically using the guidance provided herein and well known in the art (see, e.g., Nucleic Acid Hybridization (B. D. Hames and S. J. Higgins. eds., 1984) and Sambrook et al., Molecular Cloning—A Laboratory Manual (3rd Ed.), Vol. 1-3, Cold Spring Harbor Laboratory, Cold Spring Harbor, N.Y., 2000). The use of oligonucleotide probes to detect nucleotide variations including single base pair differences in sequence is described in, for example, Conner et al., 1983, *Proc. Natl. Acad. Sci. USA*, 80:278-282, and U.S. Pat. Nos. 5,468,613 and 5,604,099, each incorporated herein by reference.

In some embodiments of the probe-based methods for determining the FRZB genotypes, multiple nucleic acid sequences from the FRZB genes which encompass the polymorphic sites are amplified and hybridized to a set of probes under sufficiently stringent hybridization conditions. The alleles present are inferred from the pattern of binding of the probes to the amplified target sequences. In this embodiment, amplification is carried out in order to provide sufficient nucleic acid for analysis by probe hybridization. Thus, primers are designed such that regions of the FRZB genes encompassing the polymorphic sites are amplified regardless of the allele present in the sample. Allele-independent amplification is achieved using primers which hybridize to conserved regions of the FRZB genes. The FRZB genes contain many invariant or monomorphic regions, and suitable allele-independent primers can be selected routinely from SEQ ID NO:1 or GenBank accession numbers NT_005100.3, NT_005265, or NT_005403.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. A preferred dot-blot detection assay is described in the examples.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A preferred reverse line-blot detection assay is described in the examples.

Probe-based genotyping can be carried out using a 5'-nuclease assay, as described in U.S. Pat. Nos. 5,210,015; 5,487,972; and 5,804,375; and Holland et al., 1988, *Proc. Natl. Acad. Sci. USA*, 88:7276-7280, each incorporated herein by reference. In the 5'-nuclease assay, labeled detection probes that hybridize within the amplified region are added during the amplification reaction mixture. The probes are modified so as to prevent the probes from acting as primers for DNA synthesis. The amplification is carried out using a DNA polymerase that possesses 5' to 3' exonuclease activity, e.g., Tth DNA polymerase. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

Any method suitable for detecting degradation product can be used in the 5'-nuclease assay. In a preferred method, the detection probes are labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

The 5'-nuclease assay can be used with allele-specific amplification primers such that the probe is used only to detect the presence of amplified product. Such an assay is carried out as described for the kinetic-PCR-based methods described above. Alternatively, the 5'-nuclease assay can be used with a target-specific probe.

Examples of other techniques that can be used for probe-based genotyping include, but are not limited to, Amplifluor™, Dye Binding-Intercalation, Fluorescence Resonance Energy Transfer (FRET), Hybridization Signal Amplification Method (HSAM), HYB Probes™, Invader/Cleavase Technology (Invader/CFLP™), Molecular Beacons™, Origen™, DNA-Based Ramification Amplification (RAM™), Rolling circle amplification (RCA™), Scorpions™, Strand displacement amplification (SDA).

The assay formats described above typically utilize labeled oligonucleotides to facilitate detection of the hybrid duplexes. Oligonucleotides can be labeled by incorporating a label detectable by spectroscopic, photochemical, biochemical, immunochemical, radiological, radiochemical or chemical means. Useful labels include $^{32}$P, fluorescent dyes, electron-dense reagents, enzymes (as commonly used in ELISAs), biotin, or haptens and proteins for which antisera or monoclonal antibodies are available. Labeled oligonucleotides of the invention can be synthesized and labeled using the techniques described above for synthesizing oligonucleotides. For example, a dot-blot assay can be carried out using probes labeled with biotin, as described in Levenson et al., 1989, in *PCR Protocols: A Guide to Methods and Applications* (Innis et al., eds., Academic Press. San Diego), pages 99-112, incorporated herein by reference. Following hybridization of the immobilized target DNA with the biotinylated probes under sequence-specific conditions, probes which remain bound are detected by first binding the biotin to avidin-horseradish peroxidase (A-HRP) or streptavidin-horseradish peroxidase (SA-HRP), which is then detected by carrying out a reaction in which the HRP catalyzes a color change of a chromogen.

Whatever the method for determining which oligonucleotides of the invention selectively hybridize to FRZB allelic sequences in a sample, the central feature of the typing method involves the identification of the FRZB alleles present in the sample by detecting the variant sequences present. Further details on genotyping of SNPs are available in the literature; see, e.g., Lindblad-Toh et al., 2000, *Nature Genetics* 24:381-386; *Plant Genotyping: The DNA Fingerprinting of Plants,* 2001, CABI Publishing; Syvanen, 2001, *Nat. Rev. Genet.* 2:930-942; Kuklin et al., 1998, *Genetic Testing* 1: 201-206; Gut, 2001, *Hum. Mutat.* 17:475-492; Ahmadian et al., 2000, *Anal. Biochem.* 280:103-110; Useche et al, 2001, *Genome Inform Ser Workshop Genome Inform* 12:194-203; Pastinen et al., 2000, *Genome Res.* 10:1031-1042; Hacia, 1999, *Nature Genet.* 22:164-167; and Chen et al., 2000, *Genome Res.* 10:549-557.

Other Markers

Other genetic markers and methods of detecting sequence polymorphisms are known in the art and can be applied to the practice of the present invention, including, but not limited to, restriction fragment length polymorphisms (RFLPs), random amplified polymorphic DNA (RAPD), arbitrary fragment length polymorphisms (AFLPs), simple sequence repeats (SSRs), single-stranded conformation polymorphisms (SSCPs), and amplified variable sequences. Discovery, detection, and genotyping of these and other types of genetic markers has been well described in the literature. See, e.g., Orita et al., 1989, *Proc. Natl. Acad. Sci. USA* 86:2766-2770; U.S. Pat. No. 6,399,855; Henry, ed., 2001, *Plant Genotyping. The DNA Fingerprinting of Plants* Wallingford: CABI Publishing; Phillips and Vasil, eds., 2001, *DNA-based Markers in Plants* Dordrecht: Kluwer Academic Publishers; Pejic et al., 1998, *Theor. App. Genet.* 97:1248-1255; Bhattramakki et al., 2002, *Plant Mol. Biol.* 48:539-47; Nickerson et al., 1997, *Nucleic Acids Res.* 25:2745-2751; Underhill et al., 1997, *Genome Res.* 7:996-1005; Shi, 2001, *Clin. Chem.* 47:164-172; Kwok, 2000, *Pharmacogenomics* 1:95-100; Rafalski et al., 2002, *Cell Mol Biol Lett* 7:471-5; Ching and Rafalski, 2002, *Cell Mol Biol Lett.* 7:803-10; Powell et al., 1996, *Mol Breeding* 2:225-238; Vos et al., 1995, *Nucl. Acids Res.* 23:4407; Becker et al., 1995, *Mol. Gen. Genet.* 249:65; Meksem et al., 1995, *Mol. Gen. Genet.* 249:74; Huys et al., 1996, *Int'l J. Systematic Bacteriol.* 46:572; Jacob et al., 1991, *Cell* 67:213; Taramino and Tingey, 1996, *Genome* 39:277-287; Condit and Hubbell, 1991, *Genome* 34:66; and Zietkiewicz et al., 1994, *Genomics* 20:176-83.

Association Analysis

Evaluation of the candidate gene FRZB for association with various phenotypes pertaining to obesity and osteoporosis is described in the Examples. In addition, design and execution of various types of association studies have been described in the art; see, e.g., Rao and Province, eds., 2001, Advances in Genetics volume 42, *Genetic Dissection of Complex Traits*; Balding et al., eds., 2001, *Handbook of Statistical Genetics*, John Wiley and Sons Ltd.; Borecki and Suarez, 2001, *Adv Genet* 42:45-66; Cardon and Bell, 2001, *Nat Rev Genet* 2:91-99; and Risch, 2000, *Nature* 405:847-856. Association studies have been used both to evaluate candidate genes for association with a phenotypic trait (e.g., Thornsberry et al., 2001, *Nature Genetics* 28:286-289) and to perform whole genome scans to identify genes that contribute to phenotypic variation.

Kits

The invention also relates to a kit comprising a container unit and components for practicing the present method. A kit can contain oligonucleotide probes specific for FRZB alleles as well as instructions for their use to determine risk for obesity and/or osteoporosis. In some cases, a kit may comprise detection probes fixed to an appropriate support membrane. The kit can also contain amplification primers for amplifying regions of the FRZB locus encompassing the polymorphic sites, as such primers are useful in the preferred embodiment of the invention. Alternatively, useful kits can contain a set of primers comprising an allele-specific primer for the specific amplification of FRZB alleles. Other optional components of the kits include additional reagents used in the genotyping methods as described herein. For example, a kit additionally can contain an agent to catalyze the synthesis of primer extension products, substrate nucleoside triphosphates, reagents for labeling and/or detecting nucleic acid (for example, an avidin-enzyme conjugate and enzyme substrate and chromogen if the label is biotin) and appropriate buffers for amplification or hybridization reactions.

One aspect of the invention provides kits for detecting presence of a first predisposing or protective polymorphism in an FRZB gene, e.g., in a nucleic acid sample of an individual whose risk for osteoporosis and/or obesity is being assessed. Thus, one general class of embodiments provides a kit including one or more first oligonucleotides capable of detecting the first polymorphism and instructions for detecting the first polymorphism with the one or more first oligonucleotides and for correlating said detection to the individual's risk for osteoporosis and/or obesity, packaged in one or more containers.

Essentially all of the features noted for the method embodiments above apply to this embodiment as well, as relevant. For example, in a preferred class of embodiments, the first polymorphism is a single nucleotide polymorphism, e.g., a SNP selected from the group consisting of: the T allele of T2303723C, the C allele of T2303723C, the C allele of C18679T, the T allele of C18679T, the G allele of G19524A, the A allele of G19524A, the T allele of T22242A, the A allele of T22242A, the A allele of A24791G, the G allele of A24791G, the C allele of C26794G, the G allele of C26794G, the G allele of G27014A, and the A allele of G27014A. Other potential SNPs include, but are not limited to, either allele of T19575G, G23043A, G23415A, and T23549C.

In one aspect, the kit can be used to detect the presence of the first polymorphism by hybridization of a nucleic acid probe to the polymorphism. Thus, in one class of embodiments, the one or more first oligonucleotides comprise at least one probe. In certain embodiments, the first oligonucleotide hybridizes under stringent conditions to a region of the FRZB gene comprising the first polymorphism. In one class of embodiments, the first polymorphism is a first single nucleotide polymorphism comprising a first nucleotide at a first nucleotide position. In this class of embodiments, under stringent conditions, the first oligonucleotide hybridizes to a region of the FRZB gene comprising the first single nucleotide polymorphism with a signal to noise ratio that is at least 2× (e.g., at least 5× or at least 10×) the signal to noise ratio at which the first oligonucleotide hybridizes to the region of the FRZB gene comprising a second nucleotide at the first nucleotide position. The first oligonucleotide is typically fully complementary to the region of the FRZB gene comprising the first polymorphism, and typically comprises at least about 10 contiguous nucleotides complementary to the FRZB gene.

To facilitate detection of the polymorphism (e.g., through detection of hybridization between the one or more first oligonucleotides and a nucleic acid comprising the polymorphism), for example, the one or more first oligonucleotides optionally comprise a label, e.g., an isotopic, fluorescent, fluorogenic, luminescent or calorimetric label. In some embodiments, the label itself directly produces a detectable signal (e.g., a fluorescent label). In other embodiments, the kit also includes a reagent that detects the label (e.g., an enzyme that cleaves a colorimetric label, a binding moiety, or the like).

In one aspect, the one or more first oligonucleotides comprise one or more primers. The primer(s) can be used to detect the polymorphism, e.g., in an allele-specific amplification or extension reaction. For example, in one class of embodiments, the first polymorphism is a first single nucleotide polymorphism comprising a first nucleotide at a first nucleotide position, and the 3' nucleotide of one of the one or more first oligonucleotides is complementary to the first nucleotide.

The primer(s) can be used to amplify a region of FRZB comprising the polymorphism, e.g., for subsequent detection of the polymorphism by hybridization, sequencing, or the like. In one class of embodiments, the one or more first oligonucleotides comprise amplification primers, wherein the amplification primers amplify a nucleic acid sequence comprising the first polymorphism. In a related class of embodiments, the one or more first oligonucleotides comprise sequencing primers that flank the first polymorphism.

The one or more first oligonucleotides are optionally immobilized on a substrate. The substrate can be, for example, a planar substrate or a beaded substrate. The oligonucleotide(s) can be arranged in an array of other oligonucleotides used to detect other polymorphisms, e.g., other polymorphisms in FRZB.

The kit can optionally be used to detect more than one polymorphism (simultaneously or sequentially). Thus, in one class of embodiments, the kit also includes one or more second oligonucleotides capable of detecting a second polymorphism (and optionally third, fourth, fifth, etc. oligonucleotides capable of detecting third, fourth, fifth, etc. polymorphisms). The second polymorphism can be at the same polymorphic site as the first or at a different polymorphic site (in FRZB or a different gene), and can be protective or predisposing.

Arrays and Systems

The invention also relates to an array, a support with immobilized oligonucleotides useful for practicing the present method. A useful array can contain oligonucleotide probes specific for FRZB alleles or certain combinations of FRZB alleles. The oligonucleotides can be immobilized on a substrate, e.g., a membrane or glass. The oligonucleotides can, but need not, be labeled. In some embodiments, the array can be a micro-array. In some embodiments, the array can comprise one or more oligonucleotides used to detect the presence of two or more FRZB alleles or certain combinations of FRZB alleles.

One general class of embodiments provides arrays for detecting presence of one or more predisposing and/or protective polymorphisms in an FRZB gene, e.g., in a nucleic acid sample of an individual whose risk for osteoporosis and/or obesity is being assessed. In one class of embodiments, the array comprises a substrate and a plurality of oligonucleotides, each of which oligonucleotides hybridizes to a region of the FRZB gene comprising at least one of the polymorphisms. The hybridization detects the presence of the polymorphism, and this detection provides an indication of the individual's risk for osteoporosis and/or obesity. Typically, the array is used for detecting the presence of a plurality of polymorphisms, e.g., multiple alleles at a single polymorphic site and/or different polymorphic sites.

Essentially all of the features noted for the method and kit embodiments above apply to this embodiment as well, as relevant. For example, the one or more polymorphisms preferably comprise one or more single nucleotide polymorphisms. For example, at least one of the one or more polymorphisms can be selected from the group consisting of: the T allele of T2303723C, the C allele of T2303723C, the C allele of C18679T, the T allele of C18679T, the G allele of G19524A, the A allele of G19524A, the T allele of T22242A, the A allele of T22242A, the A allele of A24791G, the G allele of A24791G, the C allele of C26794G, the G allele of C26794G, the G allele of G27014A, and the A allele of G27014A. Other potential SNPs include, but are not limited to, either allele of T19575G, G23043A, G23415A, and T23549C.

In one class of embodiments in which the array can be used to detect presence of one or more SNPs, each of the oligonucleotides in the array hybridizes under stringent conditions to a region of the FRZB gene comprising one of the single nucleotide polymorphisms with a signal to noise ratio that is at least 2× (e.g., at least 5× or at least 10×) that at which the oligonucleotide hybridizes to a region of the FRZB gene comprising any of the remaining single nucleotide polymorphisms. Typically, one oligonucleotide is used to detect one SNP; that is, each of the oligonucleotides typically hybridizes to a distinct single nucleotide polymorphism.

As noted, the plurality of oligonucleotides are immobilized on a substrate, e.g., a planar substrate, a membrane, a glass slide, or the like. Typically, each of the plurality of oligonucleotides is immobilized at a known, pre-determined position on the substrate.

To facilitate detection of polymorphisms by specific hybridization with the oligonucleotides, each of the plurality of oligonucleotides is typically fully complementary to a region of the FRZB gene comprising one of the polymorphisms, and each of the plurality of oligonucleotides typically comprises at least about 10 contiguous nucleotides complementary to the FRZB gene. Each of the plurality of oligonucleotides optionally comprises a label, e.g., a label that facilitates detection of hybridization between the oligonucleotides and the polymorphisms.

The array is optionally part of a system. Thus, one class of embodiments provides a system comprising an array of the invention and system instructions that correlate the detection of the presence of one or more predisposing or protective polymorphisms to the individual's risk for osteoporosis and/or obesity. Systems, e.g., digital systems, are described in greater detail below.

In an array on a substrate, each oligonucleotide is typically bound (e.g., electrostatically or covalently bound, directly or via a linker) to the substrate at a unique location. Methods of making, using, and analyzing such arrays (e.g., microarrays) are well known in the art. See, e.g., Wang et al., 1998, *Science* 280:1077-82; Lockhart and Winzeler, 2000, *Nature* 405:827-836; and Scherf et al., 2000, *Nat Genet.* 24:236-44. Arrays can be formed (e.g., printed), for example, using commercially available instruments such as a GMS 417 Arrayer (Affymetrix, Santa Clara, Calif.). Suitable solid supports are commercially readily available. For example, a variety of membranes (e.g., nylon, PVDF, and nitrocellulose membranes) are commercially available, e.g., from Sigma-Aldrich, Inc. As another example, surface-modified and pre-coated slides with a variety of surface chemistries are commercially available, e.g., from TeleChem International, Corning, Inc. (Corning, N.Y.), or Greiner Bio-One, Inc. For example, silanated and silyated slides with free amino and aldehyde groups, respectively, are available and permit covalent coupling of molecules (e.g., oligos) to the slides. Slides with surface streptavidin are available and can bind biotinylated oligos. In addition, services that produce arrays of nucleic acids of the customer's choice are commercially available, e.g., from TeleChem International.

Digital Systems

In general, various automated systems can be used to perform some or all of the method steps as noted herein. In addition to practicing some or all of the method steps herein, digital or analog systems, e.g., comprising a digital or analog computer, can also control a variety of other functions such as a user viewable display (e.g., to permit viewing of method results by a user) and/or control of output features.

For example, certain of the methods described above are optionally implemented via a computer program or programs (e.g., that correlate detection of the presence of one or more predisposing or protective polymorphisms to an individual's risk for osteoporosis and/or obesity). Thus, the present invention provides digital systems, e.g., computers, computer readable media, and/or integrated systems comprising instructions (e.g., embodied in appropriate software) for performing the methods herein. For example, a digital system comprising instructions for correlating detection of the presence of one or more predisposing or protective polymorphisms to an individual's risk for osteoporosis and/or obesity, as described herein, is a feature of the invention. The digital system can also include information (data) corresponding to individual genotypes for a set of genetic markers, phenotypic values, and/or the like. The system can also aid in detection of the one or more polymorphisms (e.g., by controlling a microarray scanner, or the like).

Standard desktop applications such as word processing software (e.g., Microsoft Word™ or Corel WordPerfect™) and/or database software (e.g., spreadsheet software such as Microsoft Excel™, Corel Quattro Pro™, or database programs such as Microsoft Access™ or Paradox™) can be adapted to the present invention by inputting data which is loaded into the memory of a digital system, and performing an operation as noted herein on the data. For example, systems can include the foregoing software having the appropriate genotypic information, associations between phenotype and genotype, etc., e.g., used in conjunction with a user interface (e.g., a GUI in a standard operating system such as a Windows, Macintosh or LINUX system) to perform any analysis noted herein, or simply to acquire data (e.g., in a spreadsheet) to be used in the methods herein.

Systems typically include, e.g., a digital computer with software for performing association analysis and/or risk prediction, as well as data sets entered into the software system comprising genotypes for a set of genetic markers, phenotypic values, and/or the like. The computer can be, e.g., a PC (Intel x86 or Pentium chip-compatible DOS,™ OS2,™ WINDOWS,™ WINDOWS NT,™ WINDOWS95,™ WINDOWS98,™ LINUX, Apple-compatible, MACINTOSH™ compatible, Power PC compatible, or a UNIX compatible (e.g., SUN™ work station) machine) or other commercially common computer which is known to one of skill. Software for performing association analysis and/or risk prediction can be constructed by one of skill using a standard programming language such as Visualbasic, Fortran, Basic, Java, or the like, according to the methods herein.

Any system controller or computer optionally includes a monitor which can include, e.g., a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of genetic marker genotype, phenotypic value, or the like in the relevant computer system.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the system to carry out any desired operation. For example, in addition to performing risk prediction, a digital system can control equipment for detecting polymorphisms according to the relevant method herein.

The invention can also be embodied within the circuitry of an application specific integrated circuit (ASIC) or programmable logic device (PLD). In such a case, the invention is embodied in a computer readable descriptor language that can be used to create an ASIC or PLD. The invention can also be embodied within the circuitry or logic processors of a variety of other digital apparatus, such as PDAs, laptop computer systems, displays, image editing equipment, etc.

Molecular Biological Techniques

Conventional techniques of molecular biology and nucleic acid chemistry, which are within the skill of the art, are fully explained in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); the series, Methods in Enzymology (Academic Press, Inc.); the series Current Protocols in Human Genetics (Dracopoli et al., eds., 1984 with quarterly updates, John Wiley & Sons, Inc.); Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000; Current Protocols in Molecular Biology, F. M. Ausubel et al., eds., Current Protocols, a joint venture between Greene Publishing Associates, Inc. and John Wiley & Sons, Inc., (supplemented through 2004); Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York); and Adas and Parks (Eds.) The Handbook of Microbiological Media (1993) CRC Press, Boca Raton, Fla., all of which are incorporated herein by reference. All patents, patent applications, and publications mentioned herein, both supra and infra, are incorporated herein by reference.

EXAMPLES

The following examples are offered to illustrate, but not to limit, the claimed invention. It is understood that the examples and embodiments described herein are for illustrative purposes only and that various modifications or changes in light thereof will be suggested to persons skilled in the art and are to be included within the spirit and to purview of this application and scope of the appended claims.

Example 1

Genotyping Protocol: Allele-specific PCR of FRZB Alleles

This example describes a method of genotyping SNPs (and/or determining the frequency of alleles in pooled DNA samples) in the FRZB locus, e.g., SNPs that are associated with obesity and/or osteoporosis. The method used was basically that of Germer, et al., *Genome Research,* 10:258-266 (2000). The method and primers were initially tested on cell lines listed in Table 2. The genotypes of these cell lines in FRZB had been previously determined by DNA sequencing for certain of the lines; other lines were genotyped by sequencing later, and some have not been sequenced to date.

Allele-specific primers and common primers were designed and tested. The allele specific PCR was performed using pairs of the primers listed in Table 2 (SEQ ID NOS:3-29). All primers are shown in the 5' to 3' orientation. In addition to the primers, the control genotype of each cell line control for particular SNPs used in the test assays are also shown in Table 2.

TABLE 2

Allele-specific Assay Information

| SNP | Cell Line Control | Control Genotype | Primer | Allele | Primer Sequences (SEQ ID NO: ) |
|---|---|---|---|---|---|
| FRZB_C18679T | GM15890 | A1/A1 | AS1 | C | ATAGTAGGAGGAGTACTGTGTCG (SEQ ID NO: 3) |
| FRZB_C18679T | GM15892 | A1/A2 | AS2 | T | AATAGTAGGAGGAGTACTGTGTCA (SEQ ID NO: 4) |
| FRZB_C1B679T | GM15891 | A2/A2 | Common | | CCCTGTGGACTATCACCTAATGTT (SEQ ID NO: 5) |
| FRZB_G19524A | GM15890 | A1/A1 | AS1 | G | ATAGGCCATCAGTTGTGC (SEQ ID NO: 6) |
| FRZB_G19524A | GM15208 | A1/A2 | AS2 | A | CATAGGCCATCAGTTGTGT (SEQ ID NO: 7) |
| FRZB_G19524A | GM15206 | A2/A2 | Common | | TGAAAGTGCTGTGCTGTTCAG (SEQ ID NO: 8) |
| FRZB_T22242A | GM15207 | A1/A1 | AS1 | T | GATCTTATTTCCTCCATCTGCT (SEQ ID NO: 9) |
| FRZB_T22242A | GM15889 | A1/A2 | AS2 | A | ATCTTATTTCCTCCATCTGCA (SEQ ID NO: 10) |
| FRZB_T22242A | GM15206 | A2/A2 | Common | | CGTGAGGGAAAGGAATGTTG (SEQ ID NO: 11) |
| FRZB_G23043A | GM15888 | A1/A1 | AS1 | G | TTGTCTTTTATCCCAGTCATTC (SEQ ID NO: 12) |
| FRZB_G23043A | GM15890 | A1/A2 | AS2 | A | TTGTCTTTTATCCCAGTCATTT (SEQ ID NO: 13) |
| FRZB_G23043A | GM13626 | A1/A2 | Common | | CATCATGGCACTTAGTCTTTATCTC (SEQ ID NO: 14) |
| FRZB_G23415A | GM15888 | A1/A1 | AS1 | G | AAAAATGTAAACCTATAAACTACACG (SEQ ID NO: 15) |
| FRZB_G23415A | GM15890 | A1/A2 | AS2 | A | GAAAAATGTAAACCTATAAACTACACA (SEQ ID NO: 16) |
| FRZB_G23415A | GM13626 | A1/A2 | Common | | TCTTGATTTCATATATGGAATGGGT (SEQ ID NO: 17) |
| FRZB_323549C | GM15204 | A1/A1 | AS1 | T | ACAGTACTTGAACAAGAAAGACTTAT (SEQ ID NO: 18) |
| FRZB_323549C | GM15889 | A1/A2 | AS2 | C | ACAGTACTTGAACAAGAAAGACTTAC (SEQ ID NO: 19) |
| FRZB_T23549C | NA14700 | A1/A2 | Common | | ACTGTTCTAAATCTTAGCTGTCCTATTC (SEQ ID NO: 20) |
| FRZB_G24791A | GM10347 | A1/A1 | AS1 | G | CTCCCTTTTGACAAATCTACTG (SEQ ID NO: 21) |
| FRZB_G24791A | GM11235 | A1/A2 | AS2 | A | TCTCCCTTTTGACAAATCTACTA (SEQ ID NO: 22) |
| FRZB_G24791A | GM13625 | A2/A2 | Common | | GAAACTACCCTCCAGTAAGTTCTTC (SEQ ID NO: 23) |
| FRZB_C26794G | GM11318 | A1/A1 | AS1 | C | TTCGGGATTTAGTTGCG (SEQ ID NO: 24) |
| FRZB_C26794G | GM10873 | A1/A2 | AS2 | G | TTCGGGATTTAGTTGCC (SEQ ID NO: 25) |
| FRZB_C26794G | NA14683 | A2/A2 | Common | | GTCTGGCAGGAACTCGAACC (SEQ ID NO: 26) |

TABLE 2-continued

Allele-specific Assay Information

| SNP | Cell Line Control | Control Genotype | Primer | Allele | Primer Sequences (SEQ ID NO: ) |
|---|---|---|---|---|---|
| FRZB_G27014A | GM05045 | A1/A1 | AS1 | G | TGGGGGCAGACTCTTAAG (SEQ ID NO: 27) |
| FRZB_G27014A | GM10873 | A1/A2 | AS2 | A | TGGGGGCAGACTCTTAAA (SEQ ID NO: 28) |
| FRZB_G27014A | NA14683 | A1/A2 | Common | | CATGATTAGTGAAATAGAAAACTCACA (SEQ ID NO: 29) |
| FRZB_T19575G | GM10347 | A1/A1 | AS1 | T | GACTGAAGAAGTCAAGTTTGAGT (SEQ ID NO: 30) |
| FRZB_T19575G | GM04340 | A1/A1 | AS2 | G | ACTGAAGAAGTCAAGTTTGAGG (SEQ ID NO: 31) |
| FRZB_T19575G | GM13626 | A1/A2 | Common | | TGAACAGCAGAGCACTTTGAT (SEQ ID NO: 32) |
| FRZB_T2303723 | GM12548 | A1/A1 | AS1 | T | GTCGGCATTCTTATCATTCA (SEQ ID NO: 33) |
| FRZB_T2303723C | GM14663 | A1/A1 | AS2 | C | CGGCATTCTTATCATTCG (SEQ ID NO: 34) |
| FRZB_T2303723C | GM14667 | A2/A2 | Common | | AATAAGTCTCATCCATACTCAACCC (SEQ ID NO: 35) |

The PCR amplification was carried out in a total reaction volume of 50 µl containing the following reagents:
- 3.5 ng purified human genomic DNA
- 0.2 µM each primer (one common primer and one allele-specific primer)
- 50 µM each dATP, dCTP, dGTP
- 25 µM each dTTP
- 75 µM each dUTP
- 10 mM Tris-HCl, pH 8.3
- 3 mM $MgCl_2$
- 0.02U UNG (Uracil-n-glycosylase)
- 4% DMSO
- 2% glycerol
- 0.2×SYBR™ Green
- 12 units CEA2 Gold™ DNA polymerase*

* developed and manufactured by Hoffmann-La Roche. 0.5% glycerol added with CEA2 Gold. 1% DMSO added with SYBR Green.

The PCR was run on the GeneAmp 5700 Sequence Detection System (ABI) measuring SYBR™ Green I (Molecular Probes, Eugene, Oreg., USA) fluorescence in realtime (Higuchi, R. et al., 1993, *Biotechnology* 11:1026-30), as follows:
- 50° C. for 2 min
- 95° C. for 12 min
- 95° C. for 20 sec
- 58° C. for 20 sec
- repeated for 45 cycles.

All of the primers shown in Table 2 used under these conditions resulted in the correct, known genotype for each SNP for the designated cell line. Thus, the genotyping assay is usable for further analysis of the SNPs. The cell lines were used as positive controls in further analyses.

Example 2

Pooling Analysis for Identifying Disease Association with Known FRZB SNPs

Pooling analysis was used to facilitate the screening of candidate genes (e.g., the FRZB gene) thought to be associated with osteoporosis and/or obesity. A large allele frequency difference between pools of DNA from patients and from controls is indicative of a possible involvement of a gene in these conditions. Instead of genotyping a very large number of samples, measuring the allele frequency of a single pool composed of equal amounts of those samples allows the rapid survey of a large number of candidate genes.

Eleven exemplary SNPs in the human FRZB gene are listed in Table 1. The allele frequencies of these SNPs were measured using allele-specific, quantitative PCR on pooled samples from the Study of Osteoporotic Fractures (SOF), using the method of Germer, et al., *Genome Research*, 10:258-266 (2000) as described in Example 1. The Study of Osteoporotic Fractures (Kado, et al., *Arch. Intern. Med.* 159: 1215-1220 (1999)) includes DNAs obtained from women age 65 or older exhibiting hip fractures, vertebral fractures, low bone mineral density (BMD) or high body mass index (BMI), as well as control samples. The study group comprises 1042 DNA samples altogether.

Allele Frequency Determination:

To measure a SNP allele frequency in a mixture of DNAs pooled from individual samples, equal aliquots of the pool are divided between two PCR reactions, each of which contains a primer pair specific to one or the other SNP allelic variant (e.g., one allele-specific primer and one common primer for each SNP, as described in Example 1). The specificity of the PCR amplification is conferred by placing the 3' end of one of the primers (the allele-specific primer) directly over and matching one or the other of the variant nucleotides. This specificity can be enhanced particularly by using the Stoffel fragment of Taq DNA polymerase or variants thereof. Ideally, only completely matched primers are extended, and only the matching allele is amplified. In practice, however, there will typically be amplification of the mismatched allele, but this will occur much less efficiently such that many more amplification cycles are needed to generate detectable levels of product. Mismatch amplification is frequently delayed by >10 cycles when amplification is monitored on a cycle-by-cycle basis using fluorescent dsDNA binding dyes such as SYBR Green I. A delay of around six cycles is adequate for the determination of allele frequencies of SNPs for which the frequency of the minor allele is greater than a few percent.

When the allele frequency is 50%, one expects that each of the two PCR amplifications will require the same number of cycles to produce the same fluorescent signal, assuming that both allele-specific primers amplify with equal efficiency. The number of cycles before a reaction crosses a predetermined threshold, the $C_t$, can be fractional. When one allele is more frequent, the amplification of that allele will reach the threshold at an earlier cycle, that is, have a smaller $C_t$. The difference in $C_t$'s between the two PCR reactions, the $\Delta C_t$, is a measure of the bias and thus of the allele frequency. A one-cycle delay means that the ratio of the amount of one allele to the other is 1:2, a two-cycle delay, 1:4, or in general, $1:2^{\Delta Ct}$. Converting a ratio to a frequency by adding the numerator to the denominator results in the equation Frequency of allele$_1$=1/($2^{\Delta Ct}$+1), Where $\Delta C_t$=($C_t$ of allele$_1$-specific PCR)-($C_t$ of allele$_2$-specific PCR).

Note that $\Delta C_t$ can be either positive or negative, depending on which specific PCR exhibits the lowest $C_t$. The "2" in the denominator is properly "1+the initial replication efficiency". However, the initial replication efficiency is usually close to 100% so that "2" is an adequate approximation. The amplification efficiencies for the two allele-specific PCRs may differ slightly. As discussed in Germer et al. (supra), this can be measured and compensated for by performing the assay on a DNA known to be heterozygous for the SNP of interest. The $\Delta C_t$ for this DNA should equal zero if the PCRs are equally efficient. Any deviation from zero indicates that they are not. This deviation can then be subtracted from all $\Delta C_t$ measurements to compensate for differential amplification efficiencies.

Each SNP except T2303723C was described by its position in the reference GenBank accession sequence NT_005100.3. This sequence (containing only 4 exons) was archived and replaced in GenBank with the more complete sequence containing 6 exons (NT_005265), which was in turn replaced by NT_005403. However, the original sequence for which the numbering was based (NT_005100.3) can be obtained from GenBank, and the first 30,000 nucleotides of this sequence are presented as SEQ ID NO:1. Thus, for example, the second SNP listed in Table 1 is found at position 18679 of NT_005100.3 (and of SEQ ID NO:1), where a "T" nucleotide is present as the complement of nucleotide 18679 of SEQ ID NO:1. The common allele has a "C" nucleotide at this position. SNP T2303723C was described by its position in the GenBank accession sequence NT_005265. The SNPs will be referred to by the SNP # (i.e., by nucleotide position in either SEQ ID NO:1 or NT_005265, as indicated above, although the nucleotide(s) indicated occupy either the indicated position or its complement, depending on the particular SNP; see FIG. 1) in the subsequent text. Similarly, the SNPs can be located in any FRZB sequence by performing a sequence alignment with the allele-specific primer sequences listed in Table 2. SNPs can also be unambiguously located in the NCBI dbSNP database through the SNP source number listed in Table 1.

The pooled samples were designated A through D (see, e.g., Table 3). The criterion for pool A was hip fracture (any incident hip fracture since baseline, excluding prior hip fracture since age 50). The criterion for pool B was vertebral fracture (incident vertebral fracture by morphometry between baseline and visit 3). The criterion for pool C was low BMD (bone mineral density, defined as having hip BMD T-score <-2.5). The criteria for pool D (the control) were no fracture since age 50 and hip BMD Z-score >1.285. The criterion for the High BMI pool was a body mass index in the highest 5% of SOF participants and the criterion for the Low BMI pool was a body mass index in the lowest 5% of SOF participants.

The pools involved combining equal amounts of DNAs from patients with each specific criterion. Pool A included 275 patient samples; pool B contained 262 patient samples; pool C included 276 patient samples; and pool D contained 278 patient samples. The High BMI pool contained 141 samples and the Low BMI pool contained 82 samples. The PCRs were performed in 4 replicates using the primers and protocol outlined in Example 1 except that the PCRs contained 10 ng purified human genomic DNA and 2 uM Rox. The averages of the four replicates were calculated, and the allele frequencies were then calculated following the method above and compared to the controls. A change in allele frequency of greater than approximately 4-5% was considered significant. The pooling results for each FRZB SNP are shown in Table 3 below.

TABLE 3

FRZB Pooling results

| Pool | Average Allele 1 Frequency (%) | | | | | | Change in Allele 1 Frequency (%) | | | |
|---|---|---|---|---|---|---|---|---|---|---|
| | A | B | C | D | Low BMI | High BMI | A − D | B − D | C − D | Low BMI − High BMI |
| FRZB_C18679T | 66.38 | 61.81 | 69.06 | 63.79 | 71.02 | 65.75 | 2.59 | −1.98 | 5.27 | 5.27 |
| FRZB_G19524A | 74.12 | 68.57 | 71.49 | 68.6 | 81.69 | 67.6 | 5.52 | −0.03 | 2.89 | 14.09 |
| FRZB_T22242A | 74.66 | 69.91 | 72.74 | 70.14 | 82.27 | 72.18 | 4.52 | −0.23 | 2.60 | 10.09 |
| FRZB_G23043A | 88.01 | 91.66 | 91.15 | 88.65 | 88.79 | 88.89 | −0.63 | 3.01 | 2.50 | −0.10 |
| FRZB_G23415A | 83.69 | 89.48 | 88.86 | 84.90 | 85.30 | 86.26 | −1.21 | 4.58 | 3.96 | −0.96 |
| FRZB_T23549C | 98.30 | 97.89 | 97.33 | 98.56 | 97.77 | 97.02 | −0.26 | −0.67 | −1.22 | 0.75 |
| FRZB_A24791G | 50.53 | 56.92 | 55.67 | 56.26 | 46.12 | 61.57 | −5.73 | 0.66 | −0.59 | −15.45 |
| FRZB_C26794G | 82.22 | 81.82 | 78.24 | 82.23 | 80.5 | 76.66 | 0.0 | −0.41 | −3.99 | 3.84 |
| FRZB_G27014A | 96.79 | 98.69 | 96.54 | 95.5 | 98.62 | 96.1 | 1.29 | 3.2 | 1.04 | 2.52 |

A Hip Fracture
B Vertebral Fracture
C Low BMD
D Control

Example 3

Individual Genotyping

Because of the significant differences in allele frequency between some osteoporotic case and control groups and between the high and low BMI groups, the individual samples were genotyped to both verify the allele frequency differences and to determine genotype frequencies in these groups. The same allele-specific protocol was used on individual DNA samples to determine their genotypes. The PCR amplifications were performed as described in Example 1. The primers used to genotype the FRZB SNPs were those listed in Table 2. These results were analyzed using Pearson's Chi-Square (or an Exact Test if the number of subjects with one of the genotypes was 10 or less) to determine whether the distribution of genotype frequencies were significantly different between the groups of individuals who had any of the osteoporotic phenotypes and controls and between the groups of individuals with high BMI (a.k.a., obesity) and low BMI.

A significant association between an increased BMI and the FRZB_T2303723C, FRZB_C18679T, FRZB_G19524A and FRZB_T22242A SNPs was demonstrated (p<0.05). A lesser association between an increased BMI and the FRZB_A24791G SNP was also demonstrated (p<0.1). The T allele of T2303723C, the T allele of C18679T, the A allele of G19524A, the A allele of T22242A, and the G allele of A24791G were each demonstrated to be associated with increased BMI (and thus, with an increased risk of obesity). The association is most statistically significant if the effect of each of these alleles is assumed to be recessive.

With respect to osteoporosis, significant associations were demonstrated between increased incidence of vertebral fracture and the FRZB_C26794G and FRZB_G27014A SNPs (p<0.05). A lesser association between increased incidence of hip fracture and the FRZB_C18679T SNP was also demonstrated (p<0.1), as well as between increased incidence of hip fracture and the FRZB_G19524A SNP (p<0.1). The C allele of C18679T, the G allele of G19524A, the C allele of C26794G, and the G allele of G27014A were each demonstrated to be associated with increased incidence of hip or vertebral fracture (and thus, with an increased risk of osteoporosis). The association is most statistically significant if the effect of each of these alleles is assumed to be recessive.

In addition, it is worth noting that after adjustment for weight and age of the patients, the A allele of A24791G is associated with an increased incidence of hip fracture (p<0.1, with the A allele assumed to be recessive). Similarly, using an alternative control group (defined as no fracture since age 50 and highest 5% hip BMD by individual 5-year age group), the T allele of T22242A is associated with an increased incidence of hip fracture. Again, the association is most statistically significant if the effect of this allele is assumed to be recessive.

Association of FRZB SNPs with Obesity in Women

This example demonstrates the association of FRZB SNPs with obesity in women.

As noted, FRZB genotyping was carried out on women from the Study of Osteoporotic Fractures (SOF), using a genotyping method essentially as described in Example 1. Table 4 lists the genotyping results for the four FRZB SNPs indicated and the numbers and percents of individuals in each BMI category for each genotype.

TABLE 4

FRZB genotype association with BMI

| | C18679T | | | | G19524A | | | |
|---|---|---|---|---|---|---|---|---|
| | BMI | No. | % | | BMI | No. | % | |
| T/T | High | 18 | 12.8 | A/A | High | 14 | 10.0 | Overall |
| | Low | 3 | 3.7 | | Low | 0 | 0.0 | Distribution |
| T/C | High | 55 | 39.0 | A/G | High | 50 | 35.5 | of G19524A |
| | | | | | | | | P = .0051 |
| | Low | 38 | 46.3 | | Low | 30 | 36.6 | Model where |

TABLE 4-continued

| C/C | High | 68 | 48.2 | G/G | High | 77 | 54.6 | 19524A is |
|---|---|---|---|---|---|---|---|---|
| | Low | 41 | 50.0 | | Low | 52 | 63.4 | recessive allele |
| | | | | | | | | P = .0032 |

Total No. high BMI = 141; Total No. low BMI = 82

| | T22242A | | | | A24791G | | |
|---|---|---|---|---|---|---|---|
| | BMI | No. | %. | | BMI | No. | % |
| A/A | High | 15 | 10.7 | G/G | High | 36 | 25.5 |
| | Low | 2 | 2.4 | | Low | 13 | 15.9 |
| A/T | High | 57 | 40.4 | G/A | High | 69 | 48.9 |
| | Low | 32 | 39.0 | | Low | 43 | 52.4 |
| T/T | High | 69 | 48.9 | A/A | High | 36 | 25.5 |
| | Low | 48 | 58.5 | | Low | 26 | 31.7 |

Statistical analysis, methods and algorithms: Association of FRZB genotypes with obesity was assessed using Pearson's Chi-Square test or, if the number of subjects with one of the genotypes was 10 or less, Fisher's Exact Test. Table 4 shows the p-values (probabilities) that the distribution of genotypes at the G19524A SNP between the high and low BMI groups could have been obtained purely by chance. This is seen to be highly unlikely. Thus there is a statistical association between G19524A and BMI. The p-value is even lower if it is assumed that the minor allele, 19524A, exerts its genetic effect in a recessive (two 19524A alleles required) mode.

Association of FRZB with Osteoporosis in SOF Samples

This example demonstrates the association of FRZB SNPs with osteoporosis in SOP samples.

Table 5 lists the genotyping results for FRZB SNP C26794G and the numbers and percents of individuals in the vertebral fracture and control category for each genotype.

TABLE 5

FRZB genotype association with vertebral fracture

C26794G (Arg -> Gly)

| | fracture | No. | % | Overall Distribution |
|---|---|---|---|---|
| G/G | No | 1 | 0.4 | P = .025 |
| | Yes | 2 | 0.8 | |
| G/C | No | 52 | 18.7 | |
| | Yes | 29 | 11.1 | |
| C/C | No | 225 | 80.9 | |
| | Yes | 231 | 88.1 | |

Total No. vertebral fracture = 262;
Total No. control = 278

Statistical analysis, methods and algorithms: Association of FRZB genotypes with osteoporosis was assessed using Pearson's Chi-Square test or, if the number of subjects with one of the genotypes was 10 or less, Fisher's Exact Test. Table 5 shows the p-value (probability) that the distribution of genotypes at C26794G between the vertebral fracture and control groups could have been obtained purely by chance. This is seen to be highly unlikely. Thus there is a statistical association between C26794G and vetebral fracture. C26794G imparts a coding (amino acid) substitution (arginine to glycine) upon the protein sequence of FRZB.

As FRZB is a small component of the complex system of genes associated with obesity and/or osteoporosis (which are thought to be related since bone and fat cells originate from branches along the same developmental pathway), the effect of the FRZB locus is expected to be variable. Other factors, such as eating habits, exercise, diet, general health and the presence of associated diseases, may exert dominating effects which, in some cases, may mask the effect of the FRZB genotypes. Furthermore, because allele frequencies at other loci relevant to weight and bone-related diseases differ between populations and, thus, populations exhibit different risks for such diseases, it is expected that the effect of the FRZB genotype may be of different magnitude in some populations. Although the contribution of the FRZB genotype may, in certain populations, be relatively minor by itself, genotyping at the FRZB locus will contribute information that is, nevertheless, useful for a characterization of an individual's predisposition towards obesity and/or osteoporosis. The FRZB genotype information may be particularly useful when combined with genotype information from other loci and/or clinical tests for obesity and/or osteoporosis, for example.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto. All references cited herein are hereby incorporated by reference in their entireties.

While the foregoing invention has been described in some detail for purposes of clarity and understanding, it will be clear to one skilled in the art from a reading of this disclosure that various changes in form and detail can be made without departing from the true scope of the invention. For example, all the techniques, apparatus and/or compositions described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for determining an individual's increased risk for obesity, wherein the individual is a human female, the method comprising: detecting the presence of an obesity-related polymorphism in a frizzled-related protein (FRZB) gene in a nucleic acid sample of the individual, wherein the obesity-related polymorphism is an A allele of G19524A of the FRZB gene wherein nucleotide position 19524 is with respect to SEQ ID NO 1 and the A allele occurs in the complement of SEQ ID NO 1, wherein the presence of said A allele of G19524A provides an indication of the individual's increased risk for obesity.

2. The method of claim 1, wherein the nucleic acid sample comprises DNA or RNA.

3. The method of claim 1, wherein the A allele of G19524A is detected by sequencing.

4. The method of claim 1, wherein the A allele of G19524A is detected by amplification.

5. The method of claim 4, wherein the amplification comprises a polymerase chain reaction or a ligase chain reaction.

6. The method of claim 1, wherein the detecting comprises:

contacting the nucleic acid sample with at least one sequence-specific oligonucleotide under conditions that allow binding of said at least one oligonucleotide to the nucleic acid sample, wherein the at least one sequence-specific oligonucleotide hybridizes under stringent conditions to a region of the FRZB gene comprising the A allele of G19524A; and, detecting the hybridization of the at least one oligonucleotide to the nucleic acid sample.

7. The method of claim 1, wherein the detecting comprises:

amplifying the nucleic acid sample, thereby providing an amplified nucleic acid sample;

contacting the amplified nucleic acid sample with at least one sequence-specific oligonucleotide under conditions that allow binding of the oligonucleotide to the amplified nucleic acid sample, wherein the at least one sequence-specific oligonucleotide hybridizes under stringent conditions to a region of the FRZB gene comprising the A allele of G19524A; and, detecting the hybridization of the at least one sequence-specific oligonucleotide to the amplified nucleic acid sample.

8. The method of claim 1, wherein detecting the presence of the A allele of G19524A comprises qualitatively detecting the presence of the A allele of G19524A.

9. The method of claim 1, wherein detecting the presence of the A allele of G19524A comprises quantitatively detecting the presence of the A allele of G19524A.

10. The method of claim 1, wherein the presence of the polymorphism inherited from one of the individual's parents provides an indication of the individual's risk for obesity, or wherein the presence of the polymorphism inherited from both of the individual's parents provides an indication of the individual's risk for obesity.

11. The method of claim 1, comprising performing at least one clinical test for obesity.

12. The method of claim 11, wherein performing the at least one clinical test for obesity comprises determining a body mass index (BMI) of the individual.

* * * * *

SEQUENCE LISTING

```
<160> NUMBER OF SEQ ID NOS: 35

<210> SEQ ID NO 1
<211> LENGTH: 30000
<212> TYPE: DNA
<213> ORGANISM: Homo sapiens
<220> FEATURE:
<221> NAME/KEY: misc_feature
<222> LOCATION: (7061)..(7160)
<223> OTHER INFORMATION: n is unidentified (a, c, g or t)
<220> FEATURE:
<221> NAME/KEY: misc_feature
<222> LOCATION: (7344)..(7344)
<223> OTHER INFORMATION: n is unidentified (a, c, g or t)
<220> FEATURE:
<221> NAME/KEY: misc_feature
<222> LOCATION: (7438)..(7438)
<223> OTHER INFORMATION: n is unidentified (a, c, g or t)
<220> FEATURE:
<221> NAME/KEY: misc_feature
<222> LOCATION: (7509)..(7608)
<223> OTHER INFORMATION: n is unidentified (a, c, g or t)
<220> FEATURE:
<221> NAME/KEY: misc_feature
<222> LOCATION: (28902)..(28902)
<223> OTHER INFORMATION: n is unidentified (a, c, g or t)
<220> FEATURE:
<221> NAME/KEY: misc_feature
<222> LOCATION: (28954)..(28954)
<223> OTHER INFORMATION: n is unidentified (a, c, g or t)

<400> SEQUENCE: 1
gaattctaga tttgccatta attttgtaca ctgaactagt cgcttgacat tgacattcat      60
tagggattgt gaagaacaaa agaaatagta atatgaagtt actgataaac ggtaaagcac     120
aatataaatg tttaacaaca acgtcattgg ggagaggacg tgtcatcctc aggacaggaa     180
ccattagcaa cacaataaaa gcaaccaaca cttatgttct aggtgctgtc ctgagtgcat     240
tttgcacatt cattattatt cccattttgg agaaaaggaa gccaaggcat atagagaagc     300
taagttactg tccaagttag cagagctagt aagaaaaaga gaattcgaag cagagcctgt     360
tctacactac actttgtccc ttaagaaatg taattcctaa ctttctagag aatctgttat     420
tctttgccta gcagattgca gttaaaggaa caaaggtttt ctcattgtat tttgaagtac     480
acttatctat ggcttaagag aataaaaggt ggcttctaga caatggattc aaagagataa     540
```

-continued

```
gagattctga cttcactgca attttgagat agtagagatt atacattcca gattctcatg    600
tccctagtct ctcggtctca gcatgcccca gcgtgaactc atcatttccc catagtcatg    660
cacttgtttc tttctagtat tttctatatt gttgaaaggt accaccatac cttagtagtc    720
caggcctggg aggcagtctt ttttttttt tttttttgag acagtctcgc tctgtcactc    780
agactggagt gcagtggcgt gatctctgct cactgcaacc tctgcctcca aggttcaagc    840
aattctcctg tctcagcctc ctgagtagct gggactacag gtgcatgcca ccacgcccag    900
ctaattttg tatttctgtt agagatgggt ttcgccatg ttggccaggc tggtctcgaa    960
ctcctgacct cagatgatct gcctgccttg gcctcgcagt gctgagatta caggtgtgag   1020
tcaccatacc tggctgtggg aagcagtctt gattctacct ttttcctcat tcccctcact   1080
caataggtat cacatgctgt ttggtctact ctgactcaaa ttcccttctc tccctctcta   1140
atgctacttt cttagtttgg accttaccat ttctcaccag gattatggcc ataggatgat   1200
aatggtctct cttatctcca gtatttcccc tccatattcc aatagacatt ttttctgaaa   1260
tgcaaatctt ttgcttaaaa tccttactaa taatatatat tttcatttag ggtaatttgt   1320
tgttagaatt cctaagttta actttctgac aataattttt tgatcaatta ttagaaaatt   1380
tttgttttct gtcttacagt tctaacaatt gacttctaag catttgtaaa agcgtagaaa   1440
cattttcctt tgaataagaa tggaagaagt aaaacactct ccttggctta gctattttga   1500
agtgattccc tttcaccaag caaagtttta ttttcactc ttatttctac ctttgaacaa   1560
taaacatttc aaatatgggc caatataatt tcttcctta tgaagacatt attttgtat   1620
gtagtttatc acatgattat tcagaaatag aaaaaccact ggcacgttac tgtaatactt   1680
gggtacattt atcatgaata aatgtttgaa tataatgaaa gtattagtaa ttaatagttt   1740
atgcccaagt tgagccaaat gttttagaat tagtgtttgt tacttgctta tctgtttgtt   1800
tgctgactgc tgtcttttct tggatattgc tttttaaata cttgctgatg attactaaac   1860
ctgggaaagt aattcattaa ttgtaattgt gggtgttata gtcctaaaat agtattaacc   1920
ccttgtttaa tttattcctg ataggaccta taaacaaaaa ggacaaagga agaatactat   1980
tttctcctag aataaataga ggcattaaat tagtttagca taaagtgtta ctacaaatgt   2040
aaaactctta tataaagtac taaattggag tgtcaataag gatatattgc taggtacagc   2100
atctctcagc acggtgttcc gctggtgcac tgttattcat tagaggctgc tttcttaatt   2160
agaacacaga aaacctttat cattactatt ttctgggatt atggcatcct aaaaagaatc   2220
aatagcaatt tctaattatt gtcacatcta ttaattgcac tggcttgaat agtccctgaa   2280
tagtaggttt ctttttctgtt gaagaattat ttagcctgca gttaaaggac atgagaatga   2340
tttctgagtg ttcgtttagg aactaaggat ttaaatatat accagttcag tgtgatatgt   2400
ccatttattg aagatgcgtt tggttttttt tttgtcatca agtcataagt gttggatgag   2460
tgcctaatat ttgcataggc tttatcatga taggatgctt atcatttaca aattttgtga   2520
aattcaaata aattattaaa ttctaaaatt ttatgcacag ttgagtattc agaagagtat   2580
ttccttataa ccacatgaaa aaataagtct catccatact caacccatga atgataagaa   2640
tgccgacctc atgacgttaa taaaaatcta cttccttcag acaattggat tcttacccaa   2700
atcaaacttg tgactgagtt agatttttat ctttaggaat tcttgaaata gatatgttat   2760
agttctttt tctgtcacct cctttcgat ttcctatgg attctagtaa cggaaactgt   2820
agaggggcaa gcagtggtga gtatatcatt atcttcctgg ttttcatttg tggtcagatt   2880
```

```
agtcattgat gtaatttaga tacttaagtc attcatgggg aagcttgtgc cctacatttt    2940
acaagtaaac ttttaaaat tccctcattt atattaattt tatttttaaa attagcacgt    3000
agtaaaattg acttttatt tggacatata gtttggtaca gatgaatttt aatattatgt    3060
agagatttat gtaaccacca ccacatcagg atacagaaca attccatcac ctcccaaaac    3120
tccttcaagc tgtatccctt tataattaca agttttccct atcttcatcc actggcaatc    3180
actcatcttt tctttatcac tatagttttc tctatttgag gttcgattgt ccatatagac    3240
agactgacag tacgcctttg agacttaacc aattgctgca tatatcaatg gtgcattcct    3300
ttttattaca gaatatttta ttacttggat gtatgaccat tgttcaccc attcactcct    3360 tcaaggaagt ttgggttgtc tccagtttgg agcaatcgcg aatagagcta ctataaacat    3420
tccagtacag gttttttgtgg gaatgtaagt ttttatttct ctaggctaaa taagtaggaa    3480
taggatcact gggttatatg gtaagtatat gtttagcttt gtaaaaagt gccaaactgt      3540 ttccaagatg gctgttcaat tttgtgctag taatgtataa gagttccagt tgttctatat    3600
ctttgcgagc ccttggtatt atcaatatat tttattgtta gccatttaa taggtatgtg       3660 ataatagctc atcatggttt taaattgcat ttccctaatg gctaatgatg ctgaatacat    3720
tttcatgtgt ttatttgcta tccacatata tgcttttttgg taaaatgttc aataattttg    3780
cccattttaa gttgggttgt tttcttaatg agttctgagg gttctttaca tattctggat    3840
acaaaaaaca tcttttggtt ttattcattt tctctattgt ttcactgtttt tcaatttat    3900 tgattatttc cttctgcttg cttgctttag aggtttattt tgcttttttct tttgtttctt    3960 agagtagaag cttatattgt gttttgagac tttttttttt tttttgagat ggagtcttgc    4020
tctgttgccc aggctggagt gccgtgatgc aatctcagct caccacaacc tccacttcct    4080
gggttcaagc aattctgcct cagcctccca actagctagg attacaggtg tgcaccacca    4140
cacccagcta attttgtat tattagtaga gacaagattt caccatgttg gccagctggt    4200
ctctaacact tgatctcagg tgatccaccc accttggcct tacagagtgc tgggattaca    4260
cacgtgagcc accatgtccg gccaagacct ttcttctaat ataatgtaat gctataaata    4320
cccatctaag aatgacttta gttgcatctc acaaattttg atagtttcat ttttcttcag    4380
ttcaaaatat tttataattt tccttgatat ttccttttgac ttgtgcatca tttgggatta    4440
tgctgtttaa tttgctgctt tttgaggatt ttcctattat ctttgctatt tttcaaattc    4500
tactgttgaa gaatatactt tgtgtgattt cagttctttt agattattta aggtttattc    4560
tctgatccag gatataatct gtcttggtga atgttccatg tacacttaga aaaaagagta    4620
ttttgctgtt gggtggaatg tcctttaaat gtcaattcaa tttagttgat taatactgtt    4680
atttagttct tttatattct tgctgatttt ctgtctacta gatctattga ttaccgagag    4740
aagggtgatt aggtctccaa atattgtgga ttttttctatt tctttttttca gtctgtcagt    4800 tttgcttcat gtatttgaa gctctgtttg gtacatactt gtttaatatt ttttatgtct    4860
tattggtgaa ttgatgtttt cattatgtag tgtccttta tccttggtaa ttttctctgc    4920
tctaaattat attttttctg atattgctat aggtaattca gctgtcattt gattagtgtt    4980
tgcagggcaa aacttttct atcctacttt taacatactt aagtcattgt gttttaaata    5040
catttcttgt agacatcata tagttgggtc tttttaaaa aatccatact gttgatcttt       5100
gtcttttgat tggtatgttt tgaccatttg cagctaatgt agttattcat atttgtattt    5160
agatctactg ttttatttc tgtttgtgcc ctctccttt tattcacatt ctcttctttc    5220
ttttggattg tatctctctc tctctctctc acacacacac acgtatgtga gatatatata    5280
```

```
tatcctcatg agataatttt atattttttc ttttaacaat tacatatctt ttaaacaact   5340
tgaggagaat agtagcctac tgtattttta cagatgtttt aatttctatt attcttcctt   5400
cttttccaac attccatact tccttctggt attctttctc ttctgttctt cagacagaag   5460
ttctgtctga agaactttct taagtatttt ttgtacttgt tttaaagcag ttctgctggc   5520
aaaaacttct tttttccttt acctgaaaat attctcattt caccttcatt cctaaaggat   5580
attttcactg catacagaat tctaggtttg cagtacattt agcacataaa aaatattcca   5640
cttccttctg gcttcaatgt ttctcatggg aaattggcag tcttgcaaat aattgtttcc   5700
ctgtaagtaa tacatcagtt ttctttggtt gcatttgatt ttttttcct gtgtctttag    5760
ttttagtgc tttaattatt acatgtctgg gcattgattc ctttgagttt accctgttta    5820
gggttatctg agcttcttga atctataaat ttataatgtt agccaaattt gagaagtgct   5880
taggaattat ttcttcaaat acttgctttt tacacaatag tctcttctat gatgatatga   5940
atgttagatc ttctgatatt gttccacagg ccccagagag gctctgttaa ttttttctcc   6000
taatctttt tctctcttgt ttagattagg taatttctat tggcctagcg acaagttcat    6060
tgactctttc gttggtcttg ttcaatctcc tactctctga aacacatcca gatagttttt   6120
atttgttagt atattttca aagttaaaag ttccatttga ttcttcatta tatttttgtat  6180
ttctttggta agactttcta tctttccatt tatttcaagg gtattcaccc ttaatttgtg   6240
aggcatttta atcatagcta ccgtaaagtc atctgtgtca cctaattgtc ttgtcccact   6300
caagtcaaca tttttttctc tacatcttca tgtgtagagt aattttgggt tgaatcctgg   6360
acattttgaa tatcatgcaa taaagctttg ggtcttgttt acttaaagtt atatggaaaa   6420
tgctgatttt cttttttaa ttttagcaac agttaaccta gttaggatta ggctgcaaat    6480
tctgactggt cttctgtggg ttgtgatttt aatgtcagtt ccatttccaa agccttcgaa   6540
gtaccttcca tatctatccc acatgtatac cactcagtgg ccagtatgag gtcagagcaa   6600
tactttatcc tacagtgcag tttttgaaat ctgtgataca ctgttttatg tcagagtcac   6660
acatgcccag gggtgacttc agtagttcat aaacaacttt acaaaatcct ttcccaggct   6720
cctttatctc tctgatctcc cttgcacttt tcagttcctt ggaattcccc cgttttggtc   6780
ctttggctag aaagctttat cctactctgt gatttgcttc ttgtgactgc tccttcctat   6840
ggggccaagt ggtgggagga cagagaaaga gagagagaga caaagtaatg gggatttgcc   6900
ccagtctttt ggaactacaa gtcctccaat cagagggtaa gattctctcc ttcatcaaag   6960
ttttgggctc ctgagggtct cccttgttgc agccgttgct gttaccacag tcccaggatg   7020
cctggaggaa tggaatgcaa gaggctgata tgttagagat nnnnnnnnnn nnnnnnnnnn   7080
nnnnnnnnnn nnnnnnnnnn nnnnnnnnnn nnnnnnnnnn nnnnnnnnnn nnnnnnnnnn   7140
nnnnnnnnnn nnnnnnnnnn gaattctacc agatgtacaa aaaagagctg gtaccatacc   7200
tactaaaatt atcccaaaaa ttgaagagga gggactcctc cccaactcac tggcaggcca   7260
gcatcatcct gataccaaaa tctgacaaca gacacaacag aaaataaaat ttcaggccaa   7320
tatcattaat gaacattgat atanaaatca tcaataaaat actttccagc cgaatccagc   7380
agcacatcat aaaagtaatc caccatgagc aagtaggctt ccttcccaga tgcaaggntg   7440
gttcacatat gcaatcataa atggtattct cactaagaga ctaagacaaa acaatgatat   7500
ctcatgagnn nnnnnnnnn nnnnnnnnnn nnnnnnnnnn nnnnnnnnnn nnnnnnnnnn   7560
nnnnnnnnnn nnnnnnnnnn nnnnnnnnnn nnnnnnnnnn nnnnnnnnga attctacagt   7620
```

```
atgtattttt gtatatgcat gtgacttcct atgcttttca ttaggctgtg tatagcagta     7680
gttttccact ttaattgcta tattgtattc tatcattgaa tgtggtacac tttattcatt     7740
ctaatgttca tggatatttg ggttgttttc agttttttgtt acaatgacta atgctgcatt    7800
tatttctaca atatgatagc tgcgatgagt accatatatt ccatttcact ttcctgtagt    7860
attttgcact gattttggtg agtatgtcct gccttataag gtgtcttatc tgtggaaatg    7920
gaacatttat tttattaagt tgtaaataag tttgaaatat caactttcat tacattggga    7980
cagttttctc tgttgacttc cactgaatct tatcatggtg atatgtttga tctgagggaa    8040
tgtctaccaa aggtgtccca acaaatattt atcccattaa atacataagt aaattaaaat    8100
tattttagaa ttgttttgtt acttatata attgataatg ttttcaata tcatgaaatc       8160
agttggaaat cattgctgtc cagtaatgtt gctatttgaa gggtcactcc ttctattatg    8220
ttttctcaac ccgaactgaa aagctcattt gtataaaact gcaattggtg ggtcaaaatt    8280
tctggccaag gacatgtata tgttaccaat ttgttccaaa gttatggtta gagtaatata    8340
gcacttcaat gtatgaaaga aagaaaacac atcaacaaca ctatcaacaa tatacaaaaa    8400
acagttcaac atgtaaaact acctagaacg aatgtggtgt tctcagagtc agtgtttact    8460
gttcgtcttt taaaaatgtt ttccagttct ctggcataat gagagtgatg aaaacaaata    8520
ggcaaaacca aagctcattc tgtttgtgaa aaaacacta acatgttcac atgttctgaa      8580
aaggaaatat aatttgttca cactcaaaaa tttatgcttt ggagaaatgt aacagctgag    8640
gttgatcatg ataaaacagg aaatgaggaa ggcatgaaaa cactgtaacc cacataagga    8700
cctctttcca aagtgtcaag ctgtttctgt ctggaatttg aaaagaaat tctttcactc     8760
tagttaatat attctttgcc tcaaagctta actattttt cttttttcttt ttttgagata     8820
atgactctga acagcatcca actgtacgtt ttactgttgc aaattcacta ttgtaataag    8880
gaatagatgc tctttatttc catagcgtgt aatatggagg aaaacaattt ttgttctatt    8940
tcacctagtc acttgatcta tcaaatcagc acacagaaaa ttaaagcaga tattcaagtg    9000
gtccaatgca aagggttttt tttaattaaa ataattccaa aaagtaattc ttccaatttt    9060
ctgctttgtg agggtgacca atttatgaac tttcacattt gaaaaacaca aatgtctcca    9120
gagcggagat agagttggta aattctgaca ctaaatatat aaatgtgacc aaattatttc    9180
ttggggcctg tttcctaata taaaatcaga ttgtattgat ctgagttccc ttctgattta    9240
tcttaaatta gggaacatta gtgtaagtca gatgctctcc cagagttttc actaacctgt    9300
tcttggcgct gttccaaagg tgctccagag aagctcctct gggtagctgc ctggtggcca    9360
ctgagcaact ggagattcct gatgactgca gctgccaggc ctgcccagcc actcccactt    9420
ttgctgacat gatttatgct tagcttgggt agtatagacc cattccctct ctttctttct     9480
attacacttc tttcctccct tctggcttac taccaatttt gggaagaagt tcagtttttt    9540
tctttggtac aaatgtttac tgactgtaga gccaacttcc acaccttatt ggaaaaaaaa    9600
ggatagacaa atagtatttt tgtgatttta cagtagctta aaactatagg attttttttc    9660
cccattactt tgcaacaact gatacttttg accagttctc tttcctaagc atttctctcc    9720
ttgagctatt acccaaattg tcctagttct tctctgcttg tccctcagct atagacagtc    9780
actgaggctc tgtgcttggc ttctgttcct ctctcctcat agggattcct cctgttggag    9840
ttcatcaagc tacataggct gaattatcat tttatgact ctagttgtga ttactctcta      9900
ggaccacatt tccctcctgt aacacttcta cctgggtact ctttgagtac ttcaaaaata    9960
atgtatttaa ttactgaagt tgttttttttt ttgtttttg ttttgttttg ttttttgag    10020
```

```
atggagtctc actctgttgc tcaggctgga gtgcaatagc acgatctcag ctcactgcaa    10080
cctccatgtc ctgggttcaa gcaattctcc tgtcttagcc tcctgagtag ctgtgattac    10140
aggcacccgc caccacgcct ggctaatttt tgtatttttta atagagaagg ggtttcacca    10200
tgttggccag gctggtctct aactcctgat ctcaggtgat ccaaccacct cagcctccca    10260
gagtgctggg attacaggcg tgagccaccg tgcccagccc tgaagtaatt gtttaattaa    10320
aactttctct tttgtaactt tctcatttaa gtatgtgaca ccattgcttt tctaagtccc    10380
tagtactgaa actttatttg gttttagtcc accgatctca ccattcatta gaaatgtaat    10440
gatttgtcct gccaaaaagc ttctgcacat caaaggaaac aatcaacaaa gtgaaaagac    10500
aatccataga atgagggaaa atatttgcaa agtatctggc aagagcttaa taaccagaat    10560
atataagcaa ctctgacaat tcaatagcaa aaacaaaaca aaaacaaca aataatctaa    10620 aaatgggcaa aagatctgag cagacatttc tcaaaagaag acttacaaat ggccaacagg    10680
tatacgaaaa cattttcaac atcactaatc agataaatgc aaatcaaaac cacagtgaga    10740
tatctcaccc cagtttgaat ggcttttatc aaaaagatgg aacaatagac ggtagcgagg    10800
atgtggaaaa aggggaactc tagtatactg ttggtgggaa tgtaaattag tatagccact    10860
aaggaaaaca atagggagtt cttcaaaaaa ctaaaaatag aactaccata tgatccagca    10920
attttattac tgggtatata tccaaaagaa agggaattaa tacattgaag aatatctgta    10980
ttccaatgtt tactgcagtg ctattcacaa tagccaaaat gtagaatcaa cctaagtgct    11040
gattagtgga tgaatggata aagagaatgt agtatatatg cacaatgaca tattgttcag    11100
ctattaaaaa aaagtgaaat cctgtcattt gaaggaaaat ggaactggag gtcattatgt    11160
taaatgaaat aagccaagcc cagaaagacc aatatcacac gttctccttc atatatggga    11220
gctaaaaaca gaaaaagtg aatctcatgg agctggagag tagatttgtg gttatcagag    11280
gctgggaatg gtagcgtgga ggagggaatg aagagaggat gattaatgag gacaaatata    11340
cagttagtta ggaggaagac ctagtgtttg atagatcagt atggagacta tagttaacaa    11400
taatctactt gtacatttca atatgtacaa taattcacat gttcacagca taagagagaa    11460
tgtttaatgt ggtggatatt accctaactt gatatttaca cattatatga atgtatgaaa    11520
atatcaatgt actctgaaaa tatgtccatc tattatgtat taataaaaa tataagggac    11580 acttactcgt atcaggcaca atatgtgcca atgacatgga atgaaagagc aaataggtga    11640
ctggcactcc ctttccttc acctcttttc aatacttggc attgagtgga cacatggtgt    11700
tctagaggct gtgaagcccc cttttctttt tgttaattga cttccttaga gtctatctca    11760
aaacaacact tcagaagtca tgagggaaaa caagcataat tgtattgact ctttctatat    11820
tttggatatt ctgaataact cttggatgca gaaaacttgt gaaaggcagt ttatttgaaa    11880
ttttccaaag acaaaagga ataaactgaa tttccttttc ttattaatat agcgttagtt    11940
ctgtcagtct taagcaattt cttttacaaa gtgcaaatta ctgtgaattg agtcctttat    12000
tacaatattt gaggtttgtt tttacagcta agttgagcaa atgttacttt tactttgtaa    12060
agccttgtta tatcgcctag gttcaccagt caacttcatc acattttcca tatactggtg    12120
taatccaaaa taaatttaa tatgatattc tttgccctgt gtataggtgt aggaaataaa    12180
tattgtttta cataggtaat gaatggttac taagtcaaga cacacttcct tttataaaaa    12240
aatgaaagaa atgtcttatt ttttgttaat aggactttat taaggtataa tttatttaca    12300
gtaaaatact acaaatctta agtgtatgct gcatttaaat tttgacaaat gtatatattt    12360
```

```
atgtaaccat catccagatc aagataaaga acatttatttt atttatttat ttatttatttt   12420
tgagacggag tcttgctctg tcgcccaggc tggagtgcag tggcgcgatc tcagctcact     12480
gcaagctcca ccccccgggt tcacaccatt ctcctgcctc agcctcccga gtagctggga     12540
ctacaggcac ctgccaccac gcccggctaa tttgttgtat ttttagtaga cggggttt      12600
caccgtgtta gccaggatgg tctcgatctc ctgacctcat gatccacccg cctcggcctc     12660
ccaaagtgct gggattacag acgtgagcca ccgcaccccg gcctaaagaa catttcttta    12720
aattgtctgg tgtcttatca cccattctgc cctgaggcaa gcacagttct gattttcatt     12780
gccatagatg ggtgtcgtta ttcagcttca cgtaaatgga agcatactgt acacacttgg     12840
gactggctgc tttggcatac catggcattt ttgagacttt gagttctgtg catcatttta    12900
ttctatttct aattgtgtaa aagtacaccc ttgtatgagc ataataccaa tatgacttct     12960
atatggttcc tagtttaata tagttgattt ctgaatctgc aggagttgtg ctgttgttgt    13020
tgttgttgtt gttcgttttc ttcccttca tcattgacac caggactcta gggttcgggt    13080
gttttgtttg tttgttaatg ccctaggaac aataagaacc tgtcggtttt ccattaagtg    13140
tccatttgat gacttgcaat tttgggaaga gggaatgtgt tccatgggt ggaatctagg     13200
gatgttttac tatcgccttg tttctagaag gatagtggaa ttgacctgct gaatggccaa   13260
gtggtatatt gcccatcttc tgttttaagg actatctgaa caagttccac catggcatcc    13320
attcctgctg ctgttttgat agctgtgatg ataaggtaga tgatccatct agtgcactga    13380
tttcttcact ttactaacct gcttgtctat tctaccccag ccactcactt ccatgagcag   13440
ttctgggcct ttcagaggtg ctagcagtgg tgccagcatt gtaatattaa ttctaagaat    13500
cccatacttt gcctgctgcc tctttacatt tcacatgatt tgatgacaca tcatcactgc   13560
tgctactgat tgttttctta ccatgttgag attacctatc catcagctac tgcttactat   13620
ctgctaagcc actggccttc ttgtctatgt gagatatcat ggtctactgc aatactgata   13680
cccttgaaga taccctcaat ttctttgctt tctcttcctc ttccatactc atctggcaaa    13740
tcccaactcc agttatttga gaaaattact caactgaggt gactggtttc actttaaatt    13800
caagatagaa aattcaaata gacaatcaag attgccaagc attcttaccc actataaggt    13860
ttgccttct atttgatgaa ataactgctt tatactttct ttgcttacat gcccacatcc    13920
tgcttttcgt agcccctcat tccccatagc tgatgacttc acttcattct tcaatgagaa    13980
ggtaaaagcc attggaaaga acaccctcat tattccacca accaatttat aaacttgtca   14040
atatcagtac ctttctctcc ttttccttct tgtgtagtgg ataaagtctt ctagctttca    14100
aagtcctatt ctctcttttg ctcagggtcc agtcatcacg ttgccagttg aatttagtgg    14160
accctttct ctctgaactc attttagctc tgagggtcat ttgacacaga ggactaccct     14220
gcttttattt tggaagacgc ttttcaatt ccacactctc ctgtatttcc ttccacatca    14280
ctggatgctg cttctcagtc tcctttatgg acttcatatt tctgtcttta tatataaaga    14340
tgtagttcct gcctagagaa ctacaactca cccaaagctt taaatatcat tttctcacgg    14400
tatattggag gccagactag tttaggtcat taagttatat gttcttatta cacatataca    14460
ttgtgtttta atttcatgtc atgtatcaca tgtgacaaat tattttgtgt gtactttctt    14520
tgttcaatgt ctttatcctc ttctggattg tctgtagtgc ccatcatgtg tcctacatgc    14580
ctatcacaga gcctggaatg tagcagatgc ccaatatttg cagaatgaat gaattcatat    14640
gtaagtgact gaaagagttc aacaaatgtt agttctcttt ccctttctca tctcatattt    14700
acagaagaat ggatacacca gagttatgga gtcagaagat actactatca gttctacaga   14760
```

```
agaaagacaa attcatggtg tgatggatgt taccagatgt taaaaattat ggaactgtta   14820
aaaattttgg aactgctcat agatacctcg tacaggcagt tggaaatata gatctagagc   14880
tcagtaaaaa agtcatagtt aaggacctgg atcttcaaat tataaaattt tattttttat   14940 atctttttaaa atgtgttgtg ttttgctcct atgtgtttta aaatggagga aaagaggaca   15000
attgggattc aggggtcaaa tgccaggata tgagacttac agtgcatctg gtaaaaatta   15060
aaatgattta aactctgatc tgattagaaa aggtcagtct tgaaaaagtt ataaaggaga   15120
ttgtaacaca aatacaattg tattttcttc tctccttccc catagttttt gacaataaat   15180
cctaagcaca gatctgaggc ttttttttcct agaaaaaaca gaaaaatatc cactcaaaca   15240
tagtagtcct ccaaagtcat ggtacatgaa aggttatgag agtttgggga tctgatgaag   15300
ttaattatag tcttacacct ctggataaga cccaaaagca ttcaatttca aacaaaggtc   15360
agggatagtt agaagttttt atcacacgta agcttgaact caaacaatgt tgcattaaat   15420
agtgacggtc cagtgagtgt catatttcat agctgtatca gggacttaga cttcttttaga  15480 tcttctaaga tcatatcaaa aatactagta tccttttgtt tttaaaaaat aaatgagcat   15540
atttgtatga gcaaaactga ataaagaagg ctaagattct tgtctcctct gaactatttt   15600
gatctttata agaagctact ctgaggcagc aaggctgttc actgctcggg cactgcgtgt   15660
atcatggggc atttcccctg agctgcagac taacttctgc gaagtactgg gcatgttaac   15720
tttgcaaact cagatttctt tctactaggg tgataaactc atgtttctat gaaataaaca   15780
gtctccaggt tcattagcag atatgtagga gatcattagt attaggagag tcactagaaa   15840
aatcaagcaa gaggagtgga aggaatgtga ggaagaacta agctgaaaat agttttctgt   15900
cctttccatg gctgctggta aatgtagcac tgcactctgt cccacaattg aaggtattgt   15960
attaatttca ggctttgagg taaatgaatt gctaatgtta aaactgccca tgtttgaaga   16020
tctctttgtc actacttagc ctattttgtc aaaaccaact cctttaactt ttaaagtatt   16080 ttttttttcct tacataaagc accaaggcag atgctaattc atttataagc ttttcttctc   16140
aacagtgaaa tacagaaaaa tcaatatcta atggttttttg tgcaaagctc agtaaataat   16200
agatttcatt ttccattcta aaaaacttgt gccattagga agttgggaga ggaagattac   16260
tagcaattaa acaagaaatg atggtaatgc tacaggcccc ccaaaaagag tatcaagaaa   16320
tcaactatag gtaataaaaa taaactgtta catctgattt agggtagcag gcacaaaaaa   16380
ggtgacagct aatgcatgca acatacctct ctctgattct tcacaatttc acagttcttg   16440
ggcttgtggg gatgtgtacg ttgatgtgtg taaacataat tcagatgagg attatgtttc   16500
agatctattg atctaagata ccctttcat gaataaccta agatatgaat ttttgggttg   16560
agtaagcata aatgagagga ggttctttca tatttgagct ttgtggatat aaactcagct   16620
tctccttatt actgttattt tatcgagcta cttgaactat acagataatt tgcttatggc   16680
aagagctagg gattgggaca tattgtccca tataaatatt taaaatatat atttagtatg   16740
gcattgtcac cttggagacc agcagaaata agaagtatat tgcagatgag caaaatttag   16800
tcccgagaat atttgcttag ctcattagct gttaggtaat agtctagcta tgtatatgta   16860
gttgtatgca tagctttgta aatgcctact tgaaatatta ctaaatcatt ttgtaatata   16920
atttaaaaaa atccctgcct ggaaagtttt atggaatcca tttgtttatg ctccaagcaa   16980
agatatgtaa gtaacaacat caaattgac tcaattcagt gacagttgct atagttttg   17040 ccaaaatttt ttatttgagc acatgcaaat ttctgaagaa ttacaaatgt gtaatttatt   17100
```

```
tacatgactt attttttgata gatatttatt tttaagtaga aaaatcacaa gtctatatat   17160
ggatgaggat aatttataaa cctaatacca taaaatttta cgtcttcaga aatattctca   17220
tctcaagaat atctctttaa aaatacatgt aacattttaa tacagaataa aatacagaac   17280
gccaaaagct aggtaacttt ttgttctctt ttaaatgata atacaatcat tttgctaata   17340
aagttatttt tggaatagtt tttgtcaaaa tagcaacaag cactaatgtt actcattgtt   17400
tattggctga gatcttcaca gaaattgtgt gctaaaaatt atcaggagaa caagggaagg   17460
agctgtgtgt ggtattgagg aattctcatt tctgtcatgg gcaagagcaa cagttgctgc   17520
tgctacctat ccccagtaga gatacttatt tctctggcag gaagggtgat actcttttcg   17580
ggactgctat gttaaagtgt attattgaca agttcaactg gaaataaaat ttattttcat   17640
tagaaaatac aagtggtcaa caaaagcttc tgccttttat tgttccccat gttaacataa   17700 aacaacttt tttttttttt gagacggggt cttactctat cacccagtct ggagtgcagt   17760
ggcttgagct tggctcactg cagctttgac ttccagggct caagtgatcc tcccaactca   17820
gtctcctgaa tagctgaaac tacaggcaca tgccaccaca ccagctgatt tttgcatttt   17880
ttgtagagac ggggttttgc cacattgccc agactggtct tgaactcctg gctaaagca   17940 atttttttc ccccaccatg ttggcctccc aaagtgagtg ctgggattac aggcgtgagc   18000
gcttgtgccc agccataaaa tgccttttaa gtgaaacttt ttttgttgat gtcctttctc   18060
taatttatgt gttcttattt cctttctgtg tcaaagaga agcacatacc atttaattt   18120 tactaaagct ttctcagggg cattatttaa agaaatcttt acatataatt aaatatttta   18180
aggtaattgt gtattatttt ctacttttat attgacatta attcctgaca atttgccatg   18240
cttatgatgt atatgtctta gctaagtaat attagctttg tagctcttct ataaaaggta   18300
taataatcta ctcttcaagg tgtcaaatga atctacccta tagatgaaac attttgagat   18360
aattagaatt gttattatta tgatggccaa aaccacaact cctttgtac caacctaata   18420 tatacataaa atatgcattc tggtcactac tcaccaaata ttgttaaaaa atgaaatttc   18480
tcttttcaaa atacctgcat aatttcctcc aacaagcaca aaaataccat tgagttgaat   18540
ggtagctatt ttacctatag aaggggctca ctgcccctct taagaacttc accaagttca   18600
ctgggttgta ataacacttg cttatctctt tgagttgctt tcagatctag gagctaatag   18660
taggaggagt actgtgtcgt ctgttaaaag taaaaaaaca ttaggtgata gtccacaggg   18720
caaaccagct acctgagcat aggcagaaaa ttgcctccca gttggtattc ataatattaa   18780
tacttccata agcataaagc atacctcttt caggattaag gggtcatgct cttctcatgc   18840 atggggtga acagcatttc ctcaggattt gggtggtttg ttgagaatgg aaactcgttc   18900
tcatgagcat actgacattg aataagagga catgtagata gaataaacat gaatgtagtt   18960
ccaggagaaa aaattcagac acacagaatt gacaagagcc ttctcaccac caaattgaga   19020
tctagtctga gcaaaaaatg tgagtctgag caaaacaaaa gaaagctaat attggaaatg   19080
tgcttataac taaaatgtgt ttttcagaac gctgtaaatg taagcctatt agagctacac   19140
agaagaccta tttccggaac aattacaact atggtaagga aaatttcatg gttgatgtat   19200
aaactgctgt gttaagagag gtgtgtggat gcacctatga ggatgtgcac atgtaaacga   19260
gtggagccat ttaagaataa ggcttaaaaa cagaaggact attttttagga gcatagtccc   19320 tctgccccga ccaattaaaa tgtctcacac gggcaaaatg cttaacactt ggttgatgtt   19380
gaagcacatc aagcagtatt gtcatcctag agccatgcac ttaagtacac agagataagt   19440
atcaagatac atgggactct tccctgcctg gaggctgaag gaggatttga gctcaagttg   19500
```

```
ggttgcatag gccatcagtt gtgcttcact gagtgaacag cagagcactt tgatgcataa    19560
ggaactgtta aaagactcaa acttgacttc ttcagtcagt ctatcccatg aaaaacactg    19620
acagatttgg aaagtaacac ttgtagaagt tgctggtatt cagcgaagga aatgtgttgt    19680
tatctagctt gacttaaaat ccgacattct aataaactaa atattaattg aagagccacc    19740
aatccaaatg tagctgacaa acttaactga aggattaaaa agcctgccat ttttgcatca    19800
gggactgtgc taagtgattt ccatacatta tctttaattt tctcagctgc cccatgagat    19860
atattaccat cttgatttta tcaatgatta tcgaacctaa gtagtcccct ctttgattgt    19920
tcacaatgta ctttggatgc tggtgtatat tttagagtca taaattcatt tatacagtca    19980
ttatatttag aaagggcaat taacagagct ttcccgttga cacataaggg actgatattt    20040
actgtattcc atatgcattt tgatttttc taatatctat ggtattaata aaaggtatgt    20100
tactatctct gcataagact attgatgttg agtcaatgag taaacatgga gattaaacag    20160
acttttacag tgaaccttat taaaataaga gttttattat tacatttatg tacgctattt    20220
taaagtatat aggatatata cagcagattt atttcttcta tacttttggg aattgaaagg    20280
agagaaatga ataagactgt aaaagttagc ttcaatatct ttcaaaatgc agtgtattaa    20340
aaaatataaa gttgaaaatt tgggtttag ttaaatctct ttaaaacaaa tccaccttgt    20400
ttcccaaatt tttcttcaat ggaattaatt tctatgtttt gcctgctact cctcttaaga    20460
ggattgtagc ttttcttagt caatgatgga tgctctttct aagtttgtaa gcttatgttt    20520
atgtaagaag tcaaatgcct ggctgctat ctaagaaccc gcttctttac agattgatgt    20580
gaagaagcct agggaaaagg gagcccttaa tttctaggag attagcttgt taagattgaa    20640
aaatgctttc tgaactttta tatactgtaa cactaagaat aaaaacatat caatttata    20700 tcagggaaat gtaattattt atatttaatt tatgtatcct attatcaagt tttattttat    20760
ctagcttctg tagtgcttca atggttgttg ctgttatttt tgttaaaaat tgaatgacaa    20820
gtcatggaaa gtgaaggtct tagagaaagt agctgaatga atatcataat aaaatgggat    20880
atggattata attaatggaa aggagcagat aatttctttt ttgtagccaa gtaatagcta    20940
agttgatcat agtttcagga ttgccatttg tctgggattt cttacagttt ctttggggaa    21000
gggaggcact caaatggtta aatagaagga agaactctga aaaggaagta tattttactt    21060
ccaaaatatt tttatcttct atatctgcat gtcaaggtgg gagcagttgg aaattcagac    21120
aaaacctcta cttcatttag attaattctg ggaaaaactc cttaagtgtt aaccaaatta    21180
cttgagtgaa aaagtaggtc ttgtagaaag atatttattt tggagtgggt acatgtgcta    21240
aacatttcta atgaaaatag tagacactgg gtaaataaat cattagtttg agaacatttg    21300
cacagttcac taatctctaa tagttgatgg atgctatgaa gcacgttcac ttaagccagg    21360
acacacaaaa atgcctgcta gctgggggttg tgaatttctc atctgattct gccaaatggc    21420
atttcaaaaa gggcaatctt atcttttgtt aaatacagaa tagggagaac atgaatagaa    21480
agaggctcca cttgccagtc aaaccaagcg aggacagttg ggtagttaca gtttgtttgc    21540
tacacgttct catacttgag gcaactaatt ctcggaagac tgaaatgtga agcttttaga    21600
attccttagt aactaatttc tgtcatgtgt gttgtactgg tagaataagt ttttgtgacg    21660
aaattggaac attaatgggg ggaatggttg attagctggt tttatatttt tcaaggatta    21720 cttttcttcta atccttata gtccaaaatc tctaaaatat gtgggaaagt actcagatta    21780
aagtggtttg caattatgtg cctaagaagt ttttgaaatg ttgactcatt tggataaacg    21840
```

```
gtgttttcct ctatataatg tccatggata gtgaactgga gcaatgaggg tactgggaga    21900
aatgccactg gcttttact gatatttta cttctttctt ggtgttttaa aacttctctt     21960
tttaaaagct catttactag aagcaggaat ctgaacaact tgactctttt aaggggaga    22020 gatacagaaa agaagcagat ctgtactttc tagattctga gtcacatact ttaactttgc   22080
aactgaaggc aatttgttgt tacattgata agtaaagcaa gtcttgtgag atagattggg   22140
tgccaatata tccattgaga gaggtagaat aatgccattg acacgtgaga atatattcca   22200
tagcacgtga gggaaggaa tgttggagtg tctgacttca atgcagatgg aggaaataag    22260
atctagtggt gaccattttt attcaagaag taaatatagc ccacttagag gagaatataa   22320
aagataatct gtactgaaca caaggaaaa aaggacctaa tatccgaaca aagaagaaaa    22380
tgtagcccac ctaaaggaga atataaaaga taatctgtac tgaccacaaa gaagaaagg    22440 agctaatatc tgaacagtga gccaagatga ggaaggtgaa aagattgcag aaccagtttg   22500
ggaacactac tgagcaggac aattttataa cattacagag gcccactact tgagaaaacc   22560
tgttaatgga cctgataaaa cagtgtcgac aaggaataaa gcatatttaa gtattaggtc   22620
ttttcatata gtaaaattaa catagtttaa attcctcttg gcagcaattg gaactgcaca   22680
tgcatatata cacatccaaa atggaatttt agagaaaaat tgtatcagat tgttgactca   22740
atctttgatt ctctaaatgg atttctcaaa agcacatgca cacacatgca taaatacatg   22800
caaatatata cacagccaca aattggaaag agagcagggc tgagcattag gtcaggtgtg   22860
ttgttttatg tcacacacta cagtctaagg caaaaatatc tggctgactt ttctgttcca   22920
ttcgttgaat atcaagtgga taagaattaa ctaaagagaa gcctactttg gcttttttg    22980 aatgggggtag ctattatgtg tcatattatt atcagctttt cttgtctttt atcccagtca  23040
tttgggctaa agttaaagag ataaagacta agtgccatga tgtgactgca gtagtggagg   23100
tgaaggagat tctaaagtcc tctctggtaa acattccacg ggacactgtc aacctctata   23160
ccagctctgg ctgcctctgc cctccactta atgttaatga ggaatatatc atcatgggct   23220
atgaagatga ggaacgttcc aggtaattca ctctttaagg atacagaata actactttgc   23280
ttatcctact ctcattaaat ttgtctctag agatgctacc ctcgcatttt tacattggga   23340
tctgtctacc ttcttgggga ttacagataa gttttagttg ggtttcttga tttcatatat   23400
ggaatgggtg tatgcgtgta gtttataggt ttacattttt cttgggagag gggccataac   23460
ttcatttgtt tcttaaaggg gtctgtgact tacaaatggt taataattac tgttctaaat   23520
cttagctgtc ctattcaaga ataaacatgt aagtcttct tgttcaagta ctgtttcctt    23580
gtacttttca gtaacaggtt ttaatttttc aaaaatgttt gcttctttca aaaatacaga   23640
ttactcttgg tggaaggctc tatagctgag aagtggaagg atcgacttgg taaaaaagtt   23700
aaggtaagcc tgtattttat gtttgaagta atacacagaa aacaaaacaa aagtagaaaa   23760
ccagccatct gtcattgaaa tgaaatagct gccttcaacc atatgagaaa tattaaaatt   23820
tagtatgcat atatttatat actccaagag ctgaatttgt ctttaatgtc tattttattt   23880
aaggaatgag ttccctgtat gtgtatcaaa gatctaacta cagttgccct aatgtctctt   23940
cacaaggagt ctagctgtag tccagtcctg gtagggtggt ttcatgttgt caggctcctt   24000
ctagcttatc actctaccat ttttaaaggc atcgctttca tactcatgtt cacctggagg   24060
tcacaagatg gctgctctgc ctctagtatc acatgtacat ttcaggcagg aaaaagagga   24120
ggtaaaaggg atttccaaga gcctcatcaa gcagttttta cttagctgca aaacaggcta   24180
gaaaatgtag tctttttaaa cctggggata ttgcttcttt gaacaaactg cagtttgtga   24240
```

```
gaaggggaga ataaatgatg ggaaggaaaa taaacaatga tgtccgatga ataaacagca    24300
attcctatgt acaaagtgta gctacattca tctgtataga agagatctga ataaattagg    24360
tccttagagc agtaatgtag ccttattttt aagccaaata actcttagat tgtggaattg    24420
atacattttt taaaatcaca tagtacagta ctgtattata gaaggttttg tttcttctta    24480
ctgcactaag caaatctgtt ttaaagaaaa gaatggggtg ggggaatgca tgggggggaca    24540 aaaaaatctc aaaggatgtg tgggtgggtg ggggagtgg gaactgtacc aaacataata    24600
catcctcttc cttctgcaag tttgaaggct tgggaaacat ttacatggta agttaaacac    24660
ccctgggcgg tttatcttat acatctggca cttgacacgg cagacacgtt tgggtttaag    24720
tgacctacaa aaatgtagag ggcattattt tgtaaggaga aactaccctc cagtaagttc    24780
ttctcccctt cagtagattt gtcaaaaggg agatgcattt caagttcaga cttgcgggca    24840
ttctctctgc atctctcttc aattagtttg gtgtttatta agaaaaaag tggctcttgt    24900 tcagtatgtt ggaatctctt actgtcttta atttggtttt ctgcttgcta atgcagaact    24960
ggaatttgtc ctaaattcct gtaccagttg gaaaagcttt caatatccct gctgcgaagc    25020
atgtaacaag gcttactgct cctcttttgg taccaaaaca atatcattgt gttgttgaca    25080
ggacacatgg cttgtttgtc ctgttttccca ttgcttcctg caatatttcc cattgttttc    25140
cgcaggggac ttgcagagtt attattgtaa agtcattat attctcagtc tggatttaaa    25200
tattctaaag gaaagaaacc aataatttga acaattttaa attcatatgc agatattgag    25260
ggctaaagag tttgggtaga aaatctcctt tggccagaat tattgagatt cctattttag    25320
ttttccagtc aattgtaaga tgtgtaaaaa gagttttatg gaggatgtta ttttttcaat    25380
cagatttgct cttagctgag ttttgctctc agtggatgaa tcataattt tataagaaac    25440 attattatgt ttttttcatg caaatggttg tttacctgag tctcttatag cagacgattc    25500
aagatgtttg gtcttccttg ggaagttgag aatcagactg ttttttaaaat atgaagacaa    25560 gattgtggag taaagaatac tgaaatgaag aattaccttc agtaacagaa aaacaataac    25620
acatttacta tgtgctaagc acttatatt tttattaatc ttcagatgta tctacttata    25680
agtagattct attatcagtt ccaacatata catgatgaaa atgaggtcta gtaagttcaa    25740
gaaacttcat acagtaagtg gtggagttag aatttgaact tgggccatct gacccaagga    25800
tctgatggtg cttgctcttt aaagtgtggt ccctggatca gcaacatagg tatcacctgg    25860
gagcttgtta gtaatgaaaa tcttcggccc tgtctcagac ctgctaaatg agaatttgca    25920
attttaacaa attccccata tgatatccgt gtttgaagtt tgggaagtac agctgtagtt    25980
cgtattccct acctatcctc atgtaatata acttccattt aacttaaatt acatgaaaat    26040
attattgaca ttgttaatat gaaatattac taaacttgat tgtgtttatt aaaaacattg    26100
ctaatacctg ctttgtaaca cttagaacga gggcaggacc ttgtctgttt tattcattgt    26160
acttagtgga tattacttag aaaaatattt ttgagacccc cccatccctc aaaaaaattt    26220 ccatttttt ttcactgctc aaatcacata gactttaaaa ggctatgttc ttatgtgtat    26280
taagagagga tgttgaaaaa tagccttccc ttcaaattct gtgtgtaaat cttccatttg    26340
ttgagtatct gtgaagcact agcctcctgt atgttacctc aggaaatacc cagagatata    26400
gggagatatt tctgtcatca tttatagaca tggacatttt aagtttaagg tttgataaga    26460
aagcattact aaatacatta tagatgttgc gcttgttaaa gtcagagaat aatgttcata    26520
ttgcatcagt tttcttgtta ccctgggaaa tagattgata cttttggaaa agtagcaaaa    26580
```

```
tgcttcagag atctgaactt gcagtctgac ccagttgtta gaatcatgga aataatgacc    26640
ctggtgatat gtgcttgtga ctattttcta ttttaaattt cacagcgctg ggatatgaag    26700
cttcgtcatc ttggactcag taaaagtgat tctagcaata gtgattccac tcagagtcag    26760
aagtctggca ggaactcgaa cccccggcaa gcacgcaact aaatcccgaa atacaaaaag    26820
taacacagtg gacttcctat taagacttac ttgcattgct ggactagcaa aggaaaattg    26880
cactattgca catcatattc tattgtttac tataaaaatc atgtgataac tgattattac    26940
ttctgtttct cttttggttt ctgcttctct cttctctcaa cccctttgta atggtttggg    27000
ggcagactct taagtatatt gtgagttttc tatttcacta atcatgagaa aaactgttct    27060
tttgcaataa taataaatta aacatgctgt taccagagcc tctttgctgg agtctccaga    27120
tgttaattta ctttctgcac cccaattggg aatgcaatat tggatgaaaa gagaggtttc    27180
tggtattcac agaaagctag atatgcctta aaacatactc tgccgatcta attacagcct    27240 tattttgta tgccttttgg gcattctcct catgcttaga aagttccaaa tgtttataaa    27300
ggtaaaatgg cagtttgaag tcaaatgtca cataggcaaa gcaatcaagc accaggaagt    27360
gtttatgagg aaacaacacc caagatgaat tattttgag actgtcagga agtaaaataa    27420
ataggagctt aagaaagaac attttgcctg attgagaagc acaactgaaa ccagtagccg    27480
ctggggtgtt aatggtagca ttcttctttt ggcaatacat ttgatttgtt catgaatata    27540
ttaatcagca ttagagaaat gaattataac tagacatctg ctgttatcac catagttttg    27600
tttaatttgc ttccttttaa ataaacccat tggtgaaagt cttttttttt ctcttctttt    27660
aaaataaatc agaattgccg tattgaccag gaaaagatta tgtatgcacg tgcaccaggg    27720
ttagttttta aaagtacatg gctccataaa aatgctgtag attacagagt gataaaatat    27780
gcaggttttt ttgtttttgt tttttctgtt gtgtgtgtgt ctgtatttgt gtacatgtgt    27840
gtccttgcac tcacacccaa gggtggatta aaatacaggc ctgcaaactg gcctgcactt    27900
tatcatttgg gatttgtgct gcttaatgct cagcgaaaaa tgtctagtaa aatgaattat    27960
ggttgtcagg agagaggtta tttcgacttt tgaaccaatt gcacatttct cattacccaa    28020
gctgtggtga gatcccaggg gctgtggtga acaaatgatg cttttataga tggtccctag    28080
cttacaatga ttcaatttac aatgcttcaa tttaacaatt tgttgactta caatgggttt    28140
atcaggttgt aacccaatgc atttcaactt acgatatttt cagtttcgaa tgggtttatc    28200
cagatgtaac cccatcgtaa atggcggagc atctgtactt ccttcctctg gcagagttcc    28260
ttagagcctg tgccaattac ttgaaagttt cattctctgc catttacatg tgtgctatta    28320
gtagaaccaa atttctaagc tgtggcgtgc tgaaaataaa atgcttatga agcaaaaatc    28380
gtgctatgtt tccttctaca aggataatca agcaaggatg aaattcattc ctgaacaaaa    28440
gtttcctaaa atggtaaata atcatctatc taaatgttct attttaaaag tgtgagctgg    28500
gtgtggtgag tgcacctgta atccccacta cttgggaggc tgaggaagga agacggctag    28560
agcccatgag gttgaagctg cagtaagcta tgattgcggc cactgtactc cagcgtaggc    28620
gatagagcat gaccctgtct ctgtaacaac aacaaaagtg tgaaagttca ttctacaaat    28680
tggagtcact catatcatac ccaactaaaa tggagttggg aggccatggg gaaaggcacc    28740
caggtccctg ttccaggaac cattttttgca gttcaacaga aaaatcacga agacctaact    28800
ctaaccttaa gataaagtta cctagctgct gccactcacc aatcagaact tgctagatcc    28860
tacaagacgc gcctgctcca gtgactttca ttcaaaacca tntagatcac cttcctctct    28920
tccccaataa aaccccagcc tttctctttg tctntgaaca caactagagg ctacactggt    28980
```

| | | |
|---|---|---|
| ttgtgtgccc agaattacaa ttccaattct tatattccca aataaaccct ttacttggag | 29040 |
| atttatctcc ctatatttaa aggtgacaga gtaagggaac attcctgcct tctgattgac | 29100 |
| tctccaaagc caacaatttc cccagcccca gaagaaaaca ttcccacctt tgcctatagg | 29160 |
| actgcatagt cttttgagct tccaaaagac cacttccaaa gggcttgcca tctgcccatt | 29220 |
| gttgctatat tctcagatgg caaggacatc tcttttgagg tgctgatgtc ctacccttaa | 29280 |
| aaggtgagtt gggtgtcact ggggagtaat gaagcgccac cgtggatgga ctgcccctga | 29340 |
| gaatctctct tcctggtatg taagcctcaa cttgagcctg aggacagagg ggtgaaagt | 29400 |
| agtgctggtg cctcagcctg ttttcctcag gctttctcac gttaactctg taaagaagga | 29460 |
| caagaattga ctacaggaga ggtttaaagg aaccgttatc tcaaatccac aaacctcaac | 29520 |
| tctctcaatg cacagtaagc aatgttaagt aaggaactct tttgatgtat aaaagctgca | 29580 |
| gatgtttcca gcttctgcag ttttttttgg ggggtggggg ttgggtaaag ggggtatgat | 29640 |
| cagtttctgt gtaggaattt gacacacttt atgcttaata taaacaaaac acggccagat | 29700 |
| tcttagattc agcagttttt tttttttta aaccacctttc cattcggtgc cattttacaa | 29760 |
| cctactgttt taccactacc atctatagtg gcaatgtttg attttgctca cctatatgag | 29820 |
| gcttctgtca gctgtttaaa catttctaat ggtataaagc ccatgaataa agtacatttg | 29880 |
| gtttttcagt ttgatagcta caatatcttc attaataaac tgtgcagacc tcttttggaa | 29940 |
| ggatggcgtg atttatcatg atggtcacgt ttctcaggag actgcaaaac catttctact | 30000 |

```
<210> SEQ ID NO 2
<211> LENGTH: 2058
<212> TYPE: DNA
<213> ORGANISM: Homo sapiens

<400> SEQUENCE: 2
```

| | | |
|---|---|---|
| gttgggaaag agcagcctgg gcggcagggg cggtggctgg agctcggtaa agctcgtggg | 60 |
| accccattgg gggaatttga tccaaggaag cggtgattgc cggggagga gaagctccca | 120 |
| gatccttgtg tccacttgca gcgggggagg cggagacggc ggagcgggcc ttttggcgtc | 180 |
| cactgcgcgg ctgcacccctg ccccatcctg ccgggatcat ggtctgcggc agcccgggag | 240 |
| ggatgctgct gctgcgggcc gggctgcttg ccctggctgc tctctgcctg ctccgggtgc | 300 |
| ccggggctcg ggctgcagcc tgtgagcccg tccgcatccc cctgtgcaag tccctgccct | 360 |
| ggaacatgac taagatgccc aaccacctgc accacagcac tcaggccaac gccatcctgg | 420 |
| ccatcgagca gttcgaaggt ctgctgggca cccactgcag ccccgatctg ctcttcttcc | 480 |
| tctgtgccat gtacgcgccc atctgcacca ttgacttcca gcacgagccc atcaagccct | 540 |
| gtaagtctgt gtgcgagcgg gcccggcagg gctgtgagcc catactcatc aagtaccgcc | 600 |
| actcgtggcc ggagaacctg gcctgcgagg agctgccagt gtacgacagg ggcgtgtgca | 660 |
| tctctcccga ggccatcgtt actgcggacg gagctgattt tcctatggat tctagtaacg | 720 |
| gaaactgtag aggggcaagc agtgaacgct gtaaatgtaa gcctattaga gctacacaga | 780 |
| agacctattt ccggaacaat tacaactatg tcattcgggc taaagttaaa gagataaaga | 840 |
| ctaagtgcca tgatgtgact gcagtagtgg aggtgaagga gattctaaag tcctctctgg | 900 |
| taaacattcc acgggacact gtcaacctct ataccagctc tggctgcctc tgccctccac | 960 |
| ttaatgttaa tgaggaatat atcatcatgg gctatgaaga tgaggaacgt tccagattac | 1020 |
| tcttggtgga aggctctata gctgagaagt ggaaggatcg actcggtaaa aaagttaagc | 1080 |

```
gctgggatat gaagcttcgt catcttggac tcagtaaaag tgattctagc aatagtgatt    1140
ccactcagag tcagaagtct ggcaggaact cgaaccccg  gcaagcacgc aactaaatcc    1200
cgaaatacaa aaagtaacac agtggacttc ctattaagac ttacttgcat tgctggacta    1260
gcaaaggaaa attgcactat tgcacatcat attctattgt ttactataaa aatcatgtga    1320
taactgatta ttacttctgt ttctcttttg gtttctgctt ctctcttctc tcaaccccctt   1380 tgtaatggtt tgggggcaga ctcttaagta tattgtgagt tttctatttc actaatcatg    1440
agaaaaactg ttcttttgca ataataataa attaaacatg ctgttaccag agcctctttg    1500
ctggagtctc cagatgttaa tttactttct gcaccccaat tgggaatgca atattggatg    1560
aaaagagagg tttctggtat tcacagaaag ctagatatgc cttaaaacat actctgccga    1620
tctaattaca gccttatttt tgtatgcctt ttgggcattc tcctcatgct tagaaagttc    1680
caaatgttta taaaggtaaa atggcagttt gaagtcaaat gtcacatagg caaagcaatc    1740
aagcaccagg aagtgtttat gaggaaacaa cacccaagat gaattatttt tgagactgtc    1800
aggaagtaaa ataaatagga gcttaagaaa gaacattttg cctgattgag aagcacaact    1860
gaaaccagta gccgctgggg tgttaatggt agcattcttc ttttggcaat acatttgatt    1920
tgttcatgaa tatattaatc agcattagag aaatgaatta taactagaca tctgctgtta    1980
tcaccatagt tttgtttaat ttgcttcctt ttaaataaac ccattggtga aagtcccaaa    2040
aaaaaaaaaa aaaaaaaa                                                  2058

<210> SEQ ID NO 3
<211> LENGTH: 23
<212> TYPE: DNA
<213> ORGANISM: Homo sapiens

<400> SEQUENCE: 3
atagtaggag gagtactgtg tcg                                            23

<210> SEQ ID NO 4
<211> LENGTH: 24
<212> TYPE: DNA
<213> ORGANISM: Homo sapiens

<400> SEQUENCE: 4
aatagtagga ggagtactgt gtca                                           24

<210> SEQ ID NO 5
<211> LENGTH: 24
<212> TYPE: DNA
<213> ORGANISM: Homo sapiens

<400> SEQUENCE: 5
ccctgtggac tatcacctaa tgtt                                           24

<210> SEQ ID NO 6
<211> LENGTH: 18
<212> TYPE: DNA
<213> ORGANISM: Homo sapiens

<400> SEQUENCE: 6
ataggccatc agttgtgc                                                  18

<210> SEQ ID NO 7
<211> LENGTH: 19
<212> TYPE: DNA
<213> ORGANISM: Homo sapiens
```

```
<400> SEQUENCE: 7
cataggccat cagttgtgt                                                19

<210> SEQ ID NO 8
<211> LENGTH: 21
<212> TYPE: DNA
<213> ORGANISM: Homo sapiens

<400> SEQUENCE: 8
tcaaagtgct ctgctgttca c                                             21

<210> SEQ ID NO 9
<211> LENGTH: 22
<212> TYPE: DNA
<213> ORGANISM: Homo sapiens

<400> SEQUENCE: 9
gatcttattt cctccatctg ct                                            22

<210> SEQ ID NO 10
<211> LENGTH: 21
<212> TYPE: DNA
<213> ORGANISM: Homo sapiens

<400> SEQUENCE: 10
atcttatttc ctccatctgc a                                             21

<210> SEQ ID NO 11
<211> LENGTH: 20
<212> TYPE: DNA
<213> ORGANISM: Homo sapiens

<400> SEQUENCE: 11
cgtgagggaa aggaatgttg                                               20

<210> SEQ ID NO 12
<211> LENGTH: 22
<212> TYPE: DNA
<213> ORGANISM: Homo sapiens

<400> SEQUENCE: 12 ttgtcttta tcccagtcat tc                                             22

<210> SEQ ID NO 13
<211> LENGTH: 22
<212> TYPE: DNA
<213> ORGANISM: Homo sapiens

<400> SEQUENCE: 13 ttgtcttta tcccagtcat tt                                             22

<210> SEQ ID NO 14
<211> LENGTH: 25
<212> TYPE: DNA
<213> ORGANISM: Homo sapiens

<400> SEQUENCE: 14
catcatggca cttagtcttt atctc                                         25

<210> SEQ ID NO 15
<211> LENGTH: 26
<212> TYPE: DNA
```

<210> SEQ ID NO 15
<211> LENGTH: 26
<212> TYPE: DNA
<213> ORGANISM: Homo sapiens

<400> SEQUENCE: 15
aaaaatgtaa acctataaac tacacg                                    26

<210> SEQ ID NO 16
<211> LENGTH: 27
<212> TYPE: DNA
<213> ORGANISM: Homo sapiens

<400> SEQUENCE: 16
gaaaaatgta aacctataaa ctacaca                                   27

<210> SEQ ID NO 17
<211> LENGTH: 25
<212> TYPE: DNA
<213> ORGANISM: Homo sapiens

<400> SEQUENCE: 17
tcttgatttc atatatggaa tgggt                                     25

<210> SEQ ID NO 18
<211> LENGTH: 26
<212> TYPE: DNA
<213> ORGANISM: Homo sapiens

<400> SEQUENCE: 18
acagtacttg aacaagaaag acttat                                    26

<210> SEQ ID NO 19
<211> LENGTH: 26
<212> TYPE: DNA
<213> ORGANISM: Homo sapiens

<400> SEQUENCE: 19
acagtacttg aacaagaaag acttac                                    26

<210> SEQ ID NO 20
<211> LENGTH: 28
<212> TYPE: DNA
<213> ORGANISM: Homo sapiens

<400> SEQUENCE: 20
actgttctaa atcttagctg tcctattc                                  28

<210> SEQ ID NO 21
<211> LENGTH: 22
<212> TYPE: DNA
<213> ORGANISM: Homo sapiens

<400> SEQUENCE: 21
ctcccttttg acaaatctac tg                                        22

<210> SEQ ID NO 22
<211> LENGTH: 23
<212> TYPE: DNA
<213> ORGANISM: Homo sapiens

<400> SEQUENCE: 22 tctcccttttt gacaaatcta cta                                      23

<210> SEQ ID NO 23
<211> LENGTH: 25

```
<212> TYPE: DNA
<213> ORGANISM: Homo sapiens

<400> SEQUENCE: 23
gaaactaccc tccagtaagt tcttc                                           25

<210> SEQ ID NO 24
<211> LENGTH: 17
<212> TYPE: DNA
<213> ORGANISM: Homo sapiens

<400> SEQUENCE: 24
ttcgggattt agttgcg                                                    17

<210> SEQ ID NO 25
<211> LENGTH: 17
<212> TYPE: DNA
<213> ORGANISM: Homo sapiens

<400> SEQUENCE: 25
ttcgggattt agttgcc                                                    17

<210> SEQ ID NO 26
<211> LENGTH: 20
<212> TYPE: DNA
<213> ORGANISM: Homo sapiens

<400> SEQUENCE: 26
gtctggcagg aactcgaacc                                                 20

<210> SEQ ID NO 27
<211> LENGTH: 18
<212> TYPE: DNA
<213> ORGANISM: Homo sapiens

<400> SEQUENCE: 27
tgggggcaga ctcttaag                                                   18

<210> SEQ ID NO 28
<211> LENGTH: 18
<212> TYPE: DNA
<213> ORGANISM: Homo sapiens

<400> SEQUENCE: 28
tgggggcaga ctcttaaa                                                   18

<210> SEQ ID NO 29
<211> LENGTH: 27
<212> TYPE: DNA
<213> ORGANISM: Homo sapiens

<400> SEQUENCE: 29
catgattagt gaaatagaaa actcaca                                         27

<210> SEQ ID NO 30
<211> LENGTH: 23
<212> TYPE: DNA
<213> ORGANISM: Homo sapiens

<400> SEQUENCE: 30
gactgaagaa gtcaagtttg agt                                             23

<210> SEQ ID NO 31
```

```
<211> LENGTH: 22
<212> TYPE: DNA
<213> ORGANISM: Homo sapiens

<400> SEQUENCE: 31
actgaagaag tcaagtttga gg                                               22

<210> SEQ ID NO 32
<211> LENGTH: 21
<212> TYPE: DNA
<213> ORGANISM: Homo sapiens

<400> SEQUENCE: 32
tgaacagcag agcactttga t                                                21

<210> SEQ ID NO 33
<211> LENGTH: 20
<212> TYPE: DNA
<213> ORGANISM: Homo sapiens

<400> SEQUENCE: 33
gtcggcattc ttatcattca                                                  20

<210> SEQ ID NO 34
<211> LENGTH: 18
<212> TYPE: DNA
<213> ORGANISM: Homo sapiens

<400> SEQUENCE: 34
cggcattctt atcattcg                                                    18

<210> SEQ ID NO 35
<211> LENGTH: 25
<212> TYPE: DNA
<213> ORGANISM: Homo sapiens

<400> SEQUENCE: 35
aataagtctc atccatactc aaccc                                            25
```